(12) United States Patent
Kennedy et al.

(10) Patent No.: US 8,361,489 B2
(45) Date of Patent: *Jan. 29, 2013

(54) IMPLANTABLE DEVICES FOR PRODUCING INSULIN

(75) Inventors: Joseph P. Kennedy, Akron, OH (US); Gabor Erdodi, Stow, OH (US)

(73) Assignee: The University of Akron, Akron, OH (US)

( * ) Notice: Subject to any disclaimer, the term of this patent is extended or adjusted under 35 U.S.C. 154(b) by 224 days.

This patent is subject to a terminal disclaimer.

(21) Appl. No.: 12/439,057

(22) PCT Filed: Aug. 29, 2007

(86) PCT No.: PCT/US2007/018975
§ 371 (c)(1),
(2), (4) Date: Oct. 12, 2009

(87) PCT Pub. No.: WO2008/027420
PCT Pub. Date: Mar. 6, 2008

(65) Prior Publication Data
US 2010/0209468 A1 Aug. 19, 2010

Related U.S. Application Data

(60) Provisional application No. 60/840,828, filed on Aug. 29, 2006.

(51) Int. Cl.
*A61F 2/02* (2006.01)
*A61K 9/22* (2006.01)
*C08G 77/00* (2006.01)

(52) U.S. Cl. ......... 424/422; 604/891.1; 528/29; 528/31; 528/32

(58) Field of Classification Search ............. 424/422; 528/29, 31, 32; 604/891.1
See application file for complete search history.

(56) References Cited

U.S. PATENT DOCUMENTS

| | | | |
|---|---|---|---|
| 5,653,687 | A | 8/1997 | Mills et al. |
| 5,713,888 | A | 2/1998 | Neuenfeldt et al. |
| 5,773,286 | A | 6/1998 | Dionne |
| 5,855,616 | A | 1/1999 | Fournier |
| 6,083,523 | A | 7/2000 | Dionne |
| 6,372,244 | B1 | 4/2002 | Antanavich |
| 6,727,322 | B2 | 4/2004 | Kennedy et al. |
| 2004/0191227 | A1 | 9/2004 | Latta |

FOREIGN PATENT DOCUMENTS

| | | |
|---|---|---|
| WO | WO9321902 | 11/1993 |
| WO | WO0132730 | 5/2001 |
| WO | WO2006073499 | 7/2006 |

OTHER PUBLICATIONS

Kennedy et al .Amphiphilic Gels with Controlled Mesh Dimensions for Insulin Delivery, in Polymer gels, ACS Symposium Series, vol. 833 chapter 19, pp. 290-299, Oct. 15, 2002.*
Kennedy et al. Journal of Polymer Science: Part A: Polymer Chemistry, vol. 43, 2951-2963, Jun. 2005.*
Kennedy et al , Polymer gels, ACS Symposium Series, vol. 833 chapter 19, pp. 290-299, Oct. 15, 2002.*
Erdodi et al Journal of Polymer Science: Part A: Polymer Chemistry, vol. 43, 3491-3501, 2005.*
He et al J Polym Sci Part B: Polym Phys 44: 1474-1481, Apr. 2006.*
Erdodi et al Journal of Polymer Science: Part A: Polymer Chemistry, vol. 43, 4953-4964, 2005.*
Erdodi, G. et. al., Amphiphilic conetworks: Definition, synthesis, applications. Progress in Polymer Science 2006; vol. 31, Issue: 1, pp. 1-18.

* cited by examiner

*Primary Examiner* — Anoop Singh
(74) *Attorney, Agent, or Firm* — Renner Kenner; Greive Bobak; Taylor Weber

(57) ABSTRACT

The present invention generally relates to implantable devices for producing insulin in diabetic animals. Some embodiments include amphiphilic biomembranes for use in biological applications (e.g., as an alternative and/or supplemental insulin source). Some embodiments also include live insulin-producing cells contained within one or more amphiphilic membranes so as to prevent or diminish an immuno-response and/or rejection by the host.

19 Claims, 16 Drawing Sheets

IMPLANTABLE DEVICES FOR PRODUCING INSULIN

RELATED APPLICATION DATA

This application claims priority to previously filed U.S. Provisional Patent Application Nos. 60/840,828, filed on Aug. 29, 2006, entitled "Implantable Devices for Producing Insulin," which is incorporated by reference herein in its entirety.

The present invention was made in the course of research that was supported by National Science Foundation (NSF) Grant DMR 02-43314. The United States government may have certain rights to the invention or inventions herein.

FIELD OF THE INVENTION

The present invention generally relates to implantable devices for producing insulin in diabetic animals. Some embodiments include amphiphilic biomembranes for use in biological applications (e.g., as an alternative and/or supplemental insulin source). Some embodiments also include live insulin-producing cells contained within one or more amphiphilic membranes so as to prevent or diminish an immuno-response and/or rejection by the host.

BACKGROUND OF THE INVENTION

Many medical deficiencies and diseases result from the inability of cells to produce normal biologically active compounds. Many of these deficiencies can be remedied by implanting a source of the needed biologically active compounds and/or pharmaceutical agents into the individual having the deficiency. A well known disease that can be remedied by implanting biological material and/or a pharmacological agent is Type I diabetes mellitus, wherein the production of insulin by pancreatic Langerhans islet cells is substantially deficient, impaired, or nonexistent.+

Type I or insulin dependent diabetes mellitus (IDDM) is a major, expensive public health problem causing renal and vascular disease, heart disease, blindness, nerve damage, major disability, and premature death. One treatment approach is the transplantation of insulin producing pancreatic islet cells (9,000 to 12,000 islets/kg), which can return blood sugar levels to normal and free patients from the need to take exogenous insulin. If blood sugars, insulin, and C-peptide levels can be normalized at an early stage of the disease, the complications of diabetes can be avoided. Major barriers to the clinical application of islet cell transplantation have been the problems of graft rejection, the scarcity of human organs, and the expense of their procurement. The medications used to prevent rejection are costly, increase the risk of infection, and can, themselves, induce hyperglycemia, hyperlipidemia, hypertension, and renal dysfunction, although progress is being made towards less toxic drug regimens.

Injection of islet cells is appealing because it is less invasive than whole organ pancreatic grafts and entails a lower morbidity rate. Transplanted human islets (allografts) have been shown to survive in the liver after administration of immunosuppressive drugs, but reliable long term function has been difficult to achieve. Injection into the liver is usually accompanied by heparinization to avoid thrombosis, which can increase the risk of ocular complications. Furthermore, human islets are a scarce and expensive cell type. Therefore, many researchers have suggested using animal cells (xenografts), particularly porcine islets. Pigs are plentiful, although porcine islets are relatively difficult to isolate and are fragile.

Unfortunately, the immunologic barriers to the successful transplantation of xenografts are even more difficult to surmount than those for the transplantation of allografts. Humans have natural pre-formed antibodies that can react with a saccharide, Gal alpha 1,3Gal(Gal), expressed on the cells of lower mammals to trigger hyperacute rejection. In addition, the complement regulatory proteins (decay accelerating factor, membrane cofactor protein, CD59) that normally help to control damage included by complement activation cannot function because they are species specific.

In light of the above hypothesis that immunoisolation of living allogeneic or xenogeneic insulin-producing islet cells by semi-permeable membranes provides a means for correcting diabetes mellitus. In order to avoid hyperacute rejection, the recipient's antibodies should be prevented from "seeing" the foreign proteins and activating complement. The encapsulating material should also reliably safeguard the patient from infectious processes (e.g., bacteria) unwittingly transferred with the animal cells. Materials used for immunoisolation should allow insulin, glucose, oxygen, and carbon dioxide to pass freely. These molecules have diameters less than 35 Angstroms (3.5 nm). Studies suggest that pore diameters of 30 nm can exclude the immigration of immunoglobulins, complement, and cytokines (e.g., tumor necrosis factor) providing immunoisolation. Unless immune tolerance can be established, such membranes should also prevent the out-migration of xeno-antigens into the host where they can activate the indirect pathway resulting in T helper cell activation. Immune graft rejection by direct cytotoxicity appears to be a major cause for loss of transplanted cells since donor cell viability is better in immune-compromised (CD4+ T cell depleted) mice. In addition, CD4+ cells secrete interferon-[gamma] that attracts and activates macrophages and NK cells. Macrophages, in turn, recruit T-cell help and initiate rejection. B-cell humoral mediated immunity also plays a role in xenograft rejection. There is, however, ample evidence that the immune response is not the sole source of xenograft failure.

Researchers, working with ovarian cell xenografts microencapsulated in HEMA (hydroxyethyl methacrylate-methyl methacrylate), found that cells began to lose function before the antibody response occurred. Other causes of graft failure include an inflammatory response to the chemistry of the encapsulating material, nutrient deficiency, accumulation of waste products and free radicals within the encapsulating material, and inadequate oxygen delivery.

In view of the foregoing, there is a need in the art for improved methods and/or implantable devices for providing insulin to treat and/or cure diabetes.

SUMMARY OF THE INVENTION

The present invention generally relates to implantable devices for producing insulin in diabetic animals. Some embodiments include amphiphilic biomembranes for use in biological applications (e.g., as an alternative and/or supplemental insulin source). Some embodiments also include live insulin-producing cells contained within one or more amphiphilic membranes so as to prevent or diminish an immuno-response and/or rejection by the host.

In one embodiment, the present relates to an implantable device for providing insulin comprising: at least one spacing member having a suitable thickness, a first face, and a second face, wherein the first face and second face are substantially parallel to one another, a first immunoisolatory membrane affixed to the first face of the at least one spacing member, and a second immunoisolatory membrane affixed to the second face of the at least one spacing member, wherein the combination of the at least one spacing member, the first immunoisolatory membrane and the second immunoisolatory membrane yield an internal volume bounded by the spacing member, the first immunoisolatory membrane and the second immunoisolatory membrane where such internal volume is capable of receiving insulin producing cells suspended in an amphiphilic network.

In another embodiment, the present invention relates to a method of using an insulin producing device comprises the steps of: Implanting the device into a diabetic mammal; and filling the internal volume with insulin producing cells suspended in an amphiphilic network.

DESCRIPTION OF THE INVENTION

Figure 1:
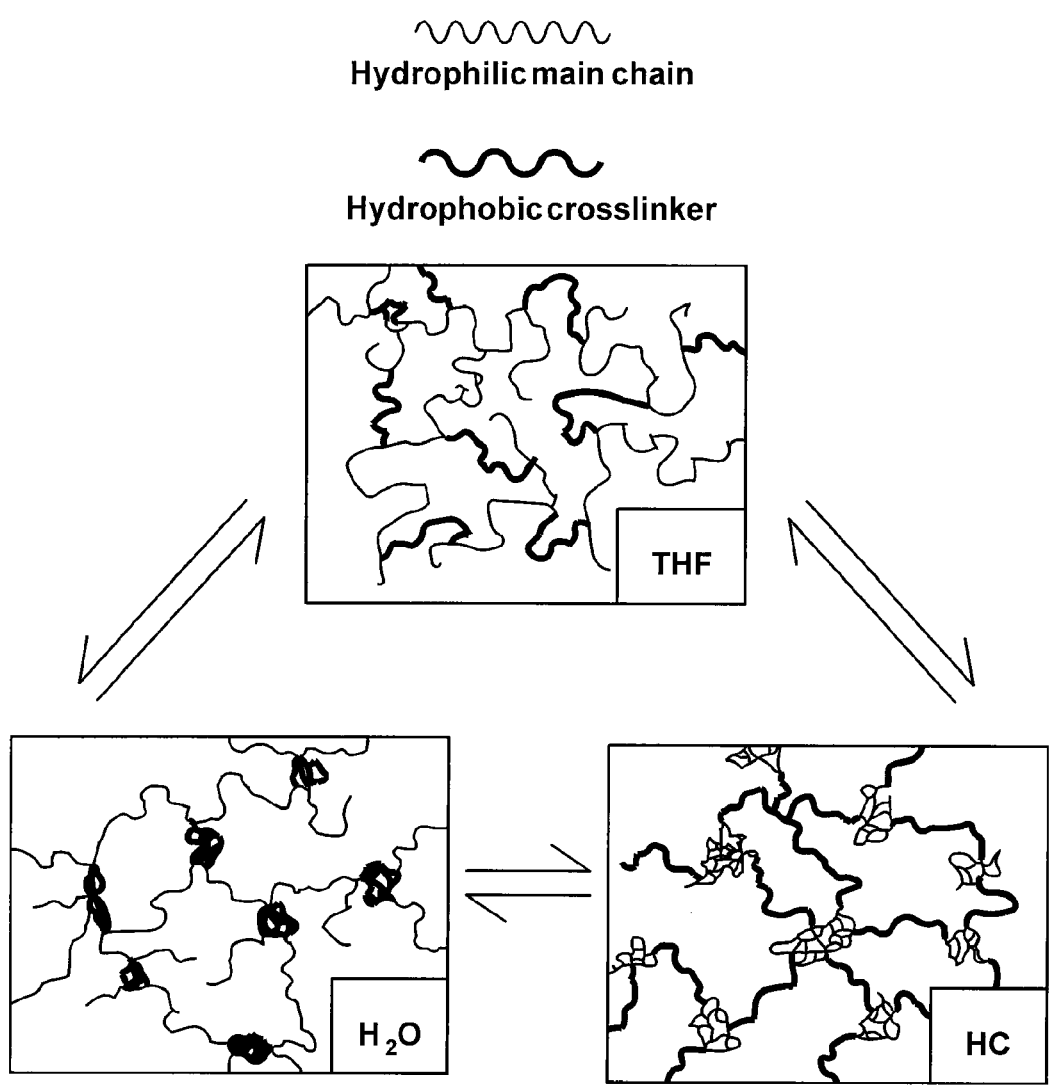
FIG. 1 is a drawing illustrating the conformational changes that the amphiphilic networks undergo in THF, hydrocarbon and water.

The present invention is generally directed to devices and materials capable of correcting, remediating, and/or mitigating diabetes in mammals. More particularly, some embodiments include implantable devices that contain insulin-producing cells. Furthermore, some embodiments include compositions and/or components that isolate the cells contained therein from immunoresponses of the host. Some such compositions and/or components include semipermeable membranes that are capable of passing insulin, gases, waste products, and the like while preventing the passage of immune system components.

Some aspects of the present invention include: (1) the synthesis of three immunoisolatory membranes having varying proportions of PEG/Y/PDMS; (2) that are capable of protecting xenografts (porcine PECs) from the immune system of the host without immunosuppressive drugs; and (3) that are biocompatible and exhibit mechanical properties amenable to implantation in vivo.

Some embodiments of the present invention are capable of correcting or mitigating diabetes in mammals such as dogs or humans. In one embodiment, correction or mitigation is achieved through implantation of a bio-artificial pancreas (BAP) 100. In one embodiment, such a BAP 100 comprises an immunoisolatory device utilizing polymeric membrane 104 adapted for xeno-immunoisolation thereby enabling the encapsulation therein of insulin producing porcine endocrine cells (PEC). Thus, some embodiments relate to correcting hyperglycemia in mammals such as dogs and/or humans without immunosuppressive drugs.

The BAP 100 device can take on any of a variety of forms provided the device is capable of containing and maintaining viable islet cells while providing insulin to a host. Many embodiments include a spacing member 102, which defines the distance between two membranes 104. For example, some embodiments include a ring or washer-shaped spacing member 102 to which immunoisolatory membranes 104 can be affixed. However, in other embodiments the ring can be substituted for any appropriate shape, as long as it provides a spacing 108 between the affixed membranes 104 sufficient to provide a thickness of up to about four islet cell diameters, i.e. about 600 microns (as measured from the outer surface of one membrane to that of the other membrane). One reason for this thickness is that oxygen must diffuse into the device in order to support cellular respiration. Thus, thinner devices are expected to be operable, but cell death is expected to increase as thickness increases above 600 microns. However, operable embodiments may exist at thicknesses above 600 microns.

In some embodiments the BAP 100 includes one or more fill ports 106, and/or vent for filling the BAP 100 device. For example, the device can include a fill port 106 that is adapted to receive a syringe needle for filling the device with islet cell culture. Such a device can also include one or more vent ports that operate in consort with the fill port, wherein displaced gases are allowed to escape through the vent as islet cells are added to the device.

In some embodiments the BAP 100 device is implanted in a diabetic host. Any of a variety of implant locations can be appropriate provided the location has sufficient blood flow and is capable of providing a sufficient means for exchanging nutrients and waste products thereby maintaining the living islet cells, and for distributing secreted insulin throughout the host's body. Some implant locations that provide such sufficient means include subcutaneous and intraperitoneal loci.

In one embodiment, the present invention utilizes a membrane 104 adapted to immunoisolate foreign cells from the immune system. In some embodiments, such immunoisolating membranes are biocompatible, biostable, non-fouling, implantable/explantable, rubbery (mechanically robust), highly $O_2$ permeable, sterilizable, soft and/or smooth. At the same time, such membranes are semi-permeable with size-controlled conduit dimensions that allow the in-diffusion of $O_2$, water, metabolites, and nutrients and the out diffusion of insulin and wastes ($CO_2$) while excluding immune cells and immunoproteins such as IgG ($M_n$=150,000 g/mole). The membranes disclosed herein meet these demanding criteria and can be synthetically tailored to the features desirable for a BAP.

Some semipermeable membranes of the present invention include amphiphilic membranes having pore size-controlled bi-continuous hydrophilic and hydrophobic domains and hydrophilic pore/channel (i.e. conduit) dimensions of about 3.0 to 4.0 nm. Some such membranes may enable survival of porcine endocrine cells (PECs) in mammals for up to three weeks or more without immunosuppression. Three immunoisolatory amphiphilic membranes can be synthesized from co-continuous covalently-linked hydrophilic poly(ethylene glycol) (PEG) and hydrophobic polydimethylsiloxane (PDMS) segments, crosslinked by tris(dimethylsilyloxy)-phenylsilane (Compound Y) units.

Some embodiments include amphiphilic water-swollen membranes having size-controlled hydrophilic pore/channel (conduit) dimensions in the about 3.0 to 4.0 nm range. Some embodiments include immunoisolatory devices comprising the foregoing membranes, and can include bio-artificial pancreas devices. Such devices benefit from properties of membranes in accordance with the present invention including biocompatible; biostable; non-fouling; implantable/explantable; mechanically robust; highly $O_2$ permeable; sterilizable; soft and smooth. At the same time the membranes of the present invention are semi-permeable with size-controlled conduit dimensions. Thus, the membranes allow the in-diffusion of $O_2$, water, metabolites, and nutrients, and the out-diffusion of insulin and wastes (e.g., $CO_2$), but exclude immune system components, such as IgG ($M_n$=150,000 g/mole).

In one embodiment, the membranes can be prepared with varying compositions of PEG/Y/PDMS (in weight percents) (40/7/53, 35/7/58, or 30/7/63) having pore sizes of about 3.0 to 4.0 nm. It should be noted that the present invention is not limited to above combinations of PEG, Compound Y, and PDMS. Rather, any suitable combination of the above-mentioned compounds can be used depending upon design criteria, to produce a membrane. BAPs are then constructed from each of the above membranes.

Some embodiments are capable of protecting xenografts (e.g. porcine PECs) from the immunoproteins of the host (e.g. dog) thereby eliminating the need for immunosuppressive drugs.

In some embodiments the membranes are biocompatible and exhibit mechanical properties that are amenable to implantation in vivo. This is accomplished by examining the tissues around the BAPs for signs of external inflammation, neo-vascularization, and fibrosis by light and electron microscopy.

Macroencapsulation entails the protection of large numbers of cells and allows cells to be implanted and removed easily. In some embodiments macroencapsulating membranes are biocompatible and have desirable mechanical properties that resist breakage.

Amphiphilic networks (i.e., networks that contain approximately equivalent quantities of randomly crosslinked co-continuous hydrophilic and hydrophobic chain elements), which swell in water, generally have desirable mechanical properties and well-defined conduits. These networks undergo conformational rearrangements rapidly in response to a contacting medium ("smart" medium-responsive microstructures). FIG. 1 illustrates the structural rearrangements that occur rapidly and reversibly upon change of the surrounding medium from tetrahydrofuran (THF) to water ($H_2O$), to hydrocarbon (HC). While not wishing to be bound to any particular theory, this adaptation to the milieu may explain the biocompatibility of certain amphiphilic networks in accordance with one embodiment. Since amphiphilic networks in accordance with the present invention are bio- and hemocompatible, and non-fouling in vivo they can be exploited for biological applications including, but not limited to, bio-artificial pancreases. Suitable embodiments of amphiphilic networks are disclosed in copending PCT application PCT/US2005/027163 and are also described below.

Amphiphilic membranes in accordance with the present invention exhibit properties that are desirable for immunoisolatory membranes. For example, some properties include (1) biocompatibility with the host (e.g. human) and guest (e.g. porcine islets); (2) hemocompatibility; (3) bio-stability for longer than six months; (4) rapid oxygen and water transport through the membrane; (5) smooth, slippery, non-clogging, non-fouling and non-thrombogenic surfaces; (6) controlled semi-permeability: Size-controlled conduit dimensions having narrow pore-size distributions (molecular weight cutoff ranges) that allow the passage of aqueous solutions of nutrients and biologically active molecules (insulin) and the exit of metabolic wastes, but exclude immunoproteins, antibodies, and white blood cells; (7) physiologically satisfactory bidirectional fluxes of glucose, insulin, nutrients, and metabolites; (8) thin membrane walls (few micrometers) to minimize diffusion paths; (9) flexible/rubbery membranes of good mechanical properties (e.g., strength, modulus, elongation, fatigue) for the implantation and explantation of large numbers (approximately $8 \times 10^5$) of islets; (10) enabling all the above properties to be maintained for long periods of time (e.g., six to twelve months); (11) simple and efficient membrane synthesis; (12) easily manufactured into sealable containers (tubes, pouches, sheets) of well-defined volumes (e.g., in the 2 to 7 mL range); (13) easily implanted and explanted; (14) sterilizable; and (15) provide all of the above properties economically.

The membranes of the present invention are comprised of fully synthetic polymers with nano-architectures expressly engineered for xeno-immunoisolation. In one embodiment, the membranes of the present invention are amphiphilic co-networks of co-continuous covalently-linked hydrophilic segments (e.g., poly(ethylene glycol) (PEG), certain acrylates, etc) and hydrophobic segments (e.g., polydimethylsiloxane (PDMS)). These nanoscale constructs ensure the rapid countercurrent transport of both $O_2$ and aqueous solutions (glucose, insulin, nutrients, metabolic wastes $CO_2$). The highly oxyphilic PDMS component, whose $O_2$ affinity/permeability is more than an order of magnitude larger than that of a typical hydro gel, ensures a sufficient $O_2$ supply to the encapsulated tissue.

In some embodiments, properties of the membranes of the present invention can be fine-tuned. For example, conduit size and the size distribution thereof can be controlled using hydrophilic and hydrophobic segments of well-defined length (i.e. molecular weight) and length distribution (i.e. molecular weight distribution). Furthermore, mechanical properties can be controlled by manipulating synthesis parameters. Additionally, in some embodiments biocompatible surfaces can be obtained by using certain biocompatible pre-polymer species.

In one embodiment, the membranes of the present invention have superior $O_2$ permeability. In this embodiment, special efforts were made to demonstrate the superiority of $O_2$ permeability of membranes in accordance with the present invention. Indeed, the $O_2$ transparency of membranes in accordance with one embodiment of the present invention is so high that the conventional Fatt method to measure $O_2$ permeability is inadequate, and the membranes of the present invention necessitated building special equipment and developing a new methodology to quantitatively determine the $O_2$ permeabilities of the membranes of the present invention. For purposes of comparison, the $O_2$ permeability of a typical hydrogel (alginate, poly(hydroxyethyl methacrylate) soft contact lens) is 10 to 20 barrer units, while that of the present invention is in the range of about 200 to 400 barrer units. Thus, some membranes of the present invention have extremely high oxygen permeability. Specific oxygen permeabilities are controlled through composition and process conditions.

In one embodiment, the present invention entails the preparation of implantable/explantable devices for xeno-transplantation of living pancreatic porcine islets into diabetic dogs, and thus will enable the elimination and/or substantial reduction of their diabetic condition. In this embodiment, the membranes of the present invention are adapted to protect the guest tissue (healthy porcine islets) from the immune system of the diabetic host and still allow molecular communication between the islets and dog thus enabling correction of hyperglycemia without the need for immunosuppression. In one example the host animals are followed for three weeks and then the devices are removed and the blood sugar measured. The blood sugar rises following explantation, thereby demonstrating that the implanted islets are responsible for correcting the hosts' hyperglycemia.

In some embodiments, the relatively small size and high $O_2$ permeability of the membranes of the present invention permit a BAP made therefrom to be implanted intraperitoneally (IP) or subcutaneously (SQ).

Some alternative embodiments include the synthesis of amphiphilic networks containing about equal amounts of hydrophilic polyacrylates, randomly crosslinked with hydrophobic polyisobutylene (PIB) segments. The microstructure and properties of these materials have been found to have surface and mechanical properties appropriate for medical applications. In some embodiments the tensile strength equal to about 0.5 to about 3.0 MPa, and the elongation is equal to about 50 to 600%.

In one embodiment, the present invention includes amphiphilic networks prepared by free radical solution copolymerization of hydrophilic monomers [N,N-dimethyl acrylamide (DMMAAm), 2-hydroxyethyl methacrylate (HEMA), N-(dimethyl-amino)ethyl methacrylate (DMAEMA) and sulfoethylmethacrylate (SEMA)] with a hydrophobic crosslinker, methacrylate-telechelic polyisobutylenes. Further development of amphiphilic membranes has shown that they are biocompatible and non-thrombogenic. Networks containing approximately 50/50% DMAEMA/PIB ($Mn_{PIB}$=10,000 g/mole) exhibit excellent biocompatibility and stability in rats, integrate well with tissue, resist bacterial contamination, and provoke little or no fibrosis or adhesion. In cell culture and protein tests the number of cells and total protein on amphiphilic networks are similar to negative controls (polyethylene, silicone rubber, glass) indicating no toxic response. Cell adhesion and anti-adhesion experiments with human monocytes have shown inhibition of monocyte adhesion for various amphiphilic networks and glass (negative control) relative to polystyrene (positive control). Amphiphilic networks made with DMAAm or HEMA with 50% PIB have also been shown to adsorb less fibrinogen, Hageman factor, and albumin from human plasma than glass, silicone rubber or polyethylene. Together with blood counts, these data suggest that amphiphilic networks in accordance with various embodiments of the present are well accepted in vivo.

By regulating the length of $M_{c,HI}$ (i.e., the molecular weight of the hydrophilic chain segment between crosslink sites) and by the overall hydrophilic/hydrophobic composition of the membranes one can achieve semi-permeability control. The molecular weight cut off (MWCO) range (conduit size control) is a function of the length of the hydrophilic and hydrophobic segments. Thus one can tailor an amphiphilic polymer to allow the rapid countercurrent diffusion of glucose and insulin, but impede or preclude the passage of large proteins such as immunoglobulins. Systematic experimentation shows that amphiphilic membranes containing approximately 50/50 PDMAAm/PIB with $M_{c,HI}$ approximately 4500 g/mole have semi-permeability and diffusion rates suitable for immunoisolation of pancreatic islets. These membranes allow the counter-current diffusion of glucose and insulin ($M_n$ equal to 180 and 5700 g/mole, respectively) but prevent the diffusion of albumin ($M_n$ approximately 66,000 g/mole). The diffusion rates of glucose and insulin are deemed appropriate for islet isolation. Pig islets placed in such semi-permeable amphiphilic polymer tubules are viable for at least 4 months and produce insulin upon glucose challenge. Further, in one embodiment a diabetic rat fitted with a BAP containing pig islets has a reversal of diabetes without immunosuppression.

In another embodiment, the amphiphilic membranes of the present invention contain well-defined (in terms of molecular weight and molecular weight distribution) polyethylene glycol (PEG) and polydimethylsiloxane (PDMS) strands co-crosslinked by hydrosilation with one or more unique oxyphilic multifunctional siloxane crosslinking agents. Membranes formed from such combinations can allow rapid glucose and insulin transport but impedes or precludes the diffusion of IgG. These diffusion embodiments are carried out with water-swollen amphiphilic membranes by the use of fluorescent-labeled insulin and IgG. In one series of related embodiments, select membranes are first incubated with IgG for several days and subsequently used to determine glucose and insulin diffusion. The rates of glucose and insulin transport through such membranes remain unchanged, demonstrating that IgG does not clog membrane conduits.

In the same series of embodiments the rate and extent of $O_2$ diffusion through membranes formed in accordance with the present invention are so high that they could even be considered for extended-wear soft contact lens applications. In addition to optical clarity, one important parameter for this application is the highest $O_2$ permeability. The membranes of the present invention are optically clear in the dry and water-swollen state.

Some membrane embodiments for BAPs, contain PEG and PDMS segments crosslinked by tris(dimethylsilyloxy)-phenylsilane (Compound Y) units. The membranes of the present invention also entail a simple, reproducible, inexpensive synthesis procedure for precision-tunable immunoisolatory membranes.

In one embodiment, the membranes of the present invention are prepared as follows. First styryl-telechelic PEG (St-PEG-St) is prepared and is end-functionalized by hydrosilation with stoichiometric quantities of Compound Y. The product PEG having SiH end groups, is further hydrosilated by vinyl-telechelic PDMS (V-PDMS-V) in the same reactor. The product of the second hydrosilation is a diblock polymer of PEG and PDMS segments separated by Compound Y units. This diblock can be easily purified (i.e., separated from the starting materials by precipitation) because it does not form micelles. Diblock purification by simple precipitation represents a significant process improvement. Subsequently, the Compound Y units are crosslinked by the addition of acid and an amphiphilic co-network in accordance with the present invention is obtained. This network is ideal because the molecular weights and molecular weight distributions of all of its strands are the same as those of the pre-polymers, and the network is tetra-functional because exactly four chains emanate from each crosslink junction.

Figure 2:
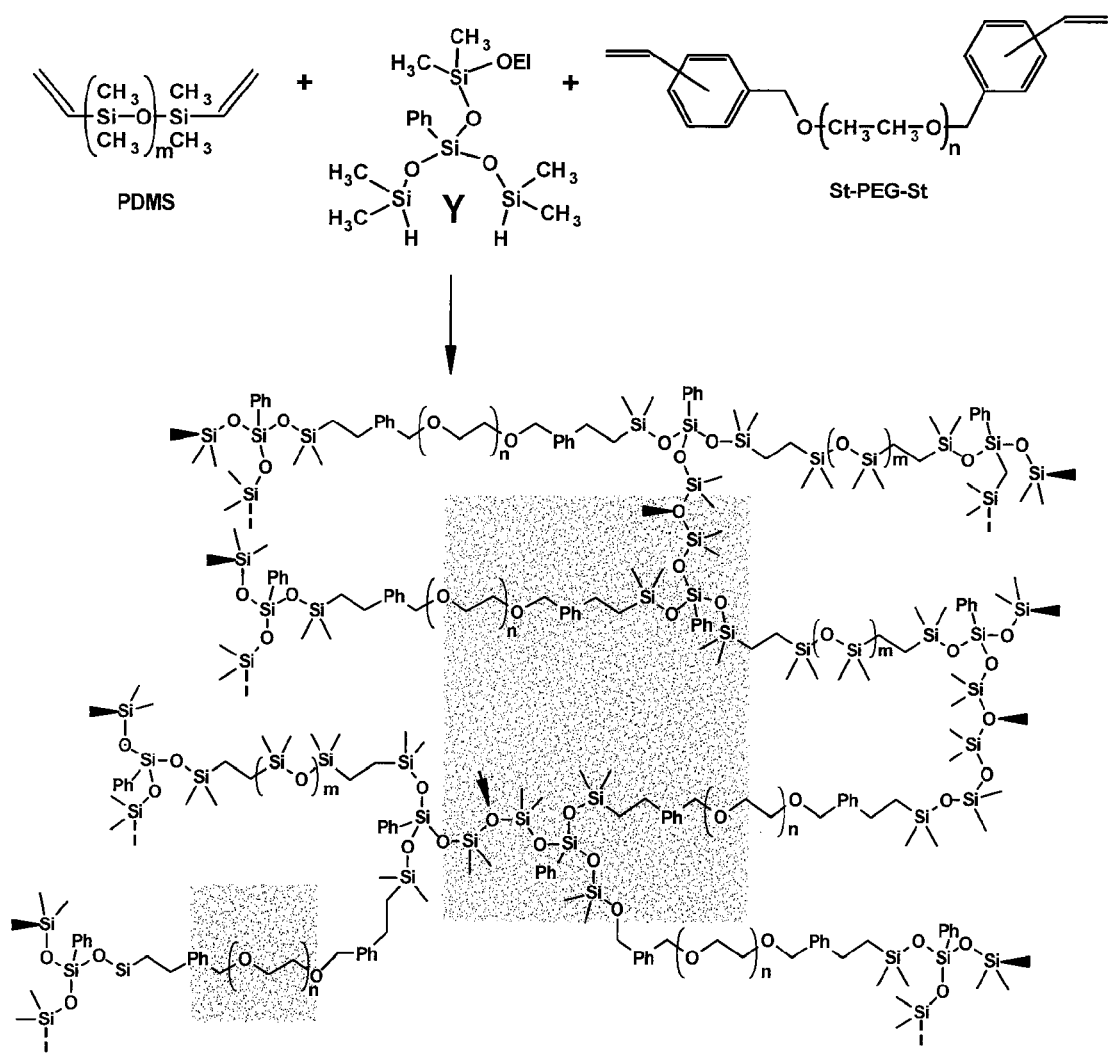
FIG. 2 is a drawing showing a generalized chemical structure of one membrane material of the present invention, and the starting materials thereof.

FIG. 2 illustrates the starting materials and the structure of one possible network in accordance with the present invention. FIG. 2 emphasizes the enchainment of the hydrophobic PDMS and Compound Y domains. Obviously, the molecular weights (lengths) and their distributions of the segments can be determined by controlling the nature of the starting materials. Further, by precisely defining the molecular weights, the overall composition of the membrane can be controlled, which in turn allows specific tailoring of conduit dimensions, water uptake, $O_2$ permeability, and mechanical properties.

In one embodiment immunoprotective tri-component amphiphilic membranes having narrow polydispersities ($M_n$ and $M_w/M_n$) PEG and PDMS strands co-crosslinked by hydrosilation with unique oxyphilic multifunctional siloxane crosslinking agents are synthesized. In some embodiments the following general procedure can be followed to prepare membranes within the scope of the present invention. Styryl-telechelic PEG having a $M_n$ equal to 4,600 g/mol, and vinyl-telechelic PDMS having a $M_n$ equal to 6,000 g/mol are synthesized and their homogeneity and structures established by GPC and NMR spectroscopy, respectively. The quantitative end-functionalization of these pre-polymers are demonstrated. The extender/crosslinker tris(dimethylsilyloxy)phenylsilane (Compound Y) is synthesized and characterized by NMR spectroscopy. Three membranes are prepared with different compositions: PEG/Y/PDMS weight percents of 40/7/53, 35/7/58, and 30/7/63.

It is estimated that approximately 12,000 islets/kg of dog weight will be necessary to reverse the diabetic state. Therefore, some embodiments utilize approximately 132,000 islet equivalents (0.23 mL cell volume) in an approximately 11 kg dog. In some embodiments the BAP 100 is a hollow disc prepared from two approximately 50 micron thick amphiphilic membranes 104, the rims of which are glued with a silicon glue to a 0.60 mm thick stainless steel or titanium ring having a 3.1 cm aperture. FIG. 4 shows a sketch of the envisioned BAP 100. The metal ring 102 provides reinforcement/dimensional stability, x-ray contrast and acts as the spacer 108 between the two membranes 104.

While FIG. 4 details a circular embodiment, any number of configurations are possible. The present invention can be configured as an oval, egg-shaped, rectangle, square, triangle, pentagon, hexagon, or any other related structure.

Islet tissue can be cultured overnight in PRMI-1640 medium containing 10% fetal calf serum, 100 IU/mL of penicillin, and 100 µg/mL of streptomycin. Before loading, the BAP 100 device is sterilized by autodaving at 120° C. for 15 minutes and allowed to cool in a tissue culture hood. The islets/cells are loaded into a syringe and injected between the two membranes 104 through a 0.4 mm wide port 106 drilled in the metal ring 102. Injection occurs under sterile conditions. After loading, the port 106 is plugged with a silicone plug, which in turn is sealed with cyanoacrylate. In this example, the volume of the device, as defined by the aperture of the ring (3.1 cm) and ring thickness (0.60 mm), is 0.46 mL. This volume is appropriate for accommodating the approximately 132,000 islets (0.23 mL volume) plus 0.23 mL of the suspending medium (alginate). The ready-to-be-used filled BAP 100 contains approximately 4.0 layers of islets. Thus, the maximum path for $O_2$ diffusion is approximately 2 islet diameters (about 300 microns).

Male 10 to 12 kg dogs are housed individually and allowed free access to dog chow and water. After a 12 hour fast, a baseline glucose tolerance test, serum C-peptide, renal function (creatinine, BUN) and liver function tests (AST, ALT, Alkaline phosphatase) is obtained. Glucose tolerance is performed by administering glucose 500 mg/kg body weight intravenously over 2 to 3 minutes. Blood glucose and insulin levels are drawn at −5, 0, 5, 10, 15, 20, 30, 45, and 60 minutes. The amount of blood required for these tests totals approximately 20 mL. Diabetes is induced by intravenous injection of alloxan (50 mg/kg) (Sigma Chemical Co. St. Louis, Mo.) and streptozotocin (STZ) (30 mg/kg) (Zanosam—obtained from the CCF pharmacy) via the cephalic vein in the foreleg. The drugs are freshly prepared aseptically as solutions, containing 100 mg/mL In trisodium citrate buffer, pH 4.5 and sterilized by filtration through 0.22 µm filters.

In one example, in vivo function of a BAP embodiment is assessed in a dog model by means of fasting blood sugars, IV glucose tolerance tests, insulin, and C-peptide levels before, after placement, and after removal of the BAP. According to this example, diabetes is chemically induced in male dogs (n=18) weighing 10 to 12 kg by a single intravenous injection of freshly prepared streptozotocin (STZ) 30 mg/kg (Zanosar) and alloxan (ALX) 50 mg/kg after a twelve hour fast. Since these drugs are known to cause hypoglycemia 8 to 16 hours after injection, the animals are kept on intravenous fluids (0.9% NaCl containing 5% dextrose) at 125 ml/hr for 24 hours. Blood glucose levels are monitored every six hours for 24 hours. Thereafter, animals are fed regular dog chow every 12 hours and receive twice daily human insulin 70/30 0.5 to 1.5 U/kg SQ (or more if glucose levels exceed 250 mg/dl) after each feeding to prevent ketosis and death. Dogs with fasting blood sugars <250 mg two weeks after chemotherapy are not utilized. Porcine C-Peptide and insulin are measured using radio-immunoassays (Linco Research, St. Charles, Mo.). The tissues around the grafts and the contents of the BAP are examined for signs of rejection (inflammatory infiltrates), neo-vascularization, cell necrosis, fibrosis, and islet cell de-granulation. No rejection occurs.

Figure 3:
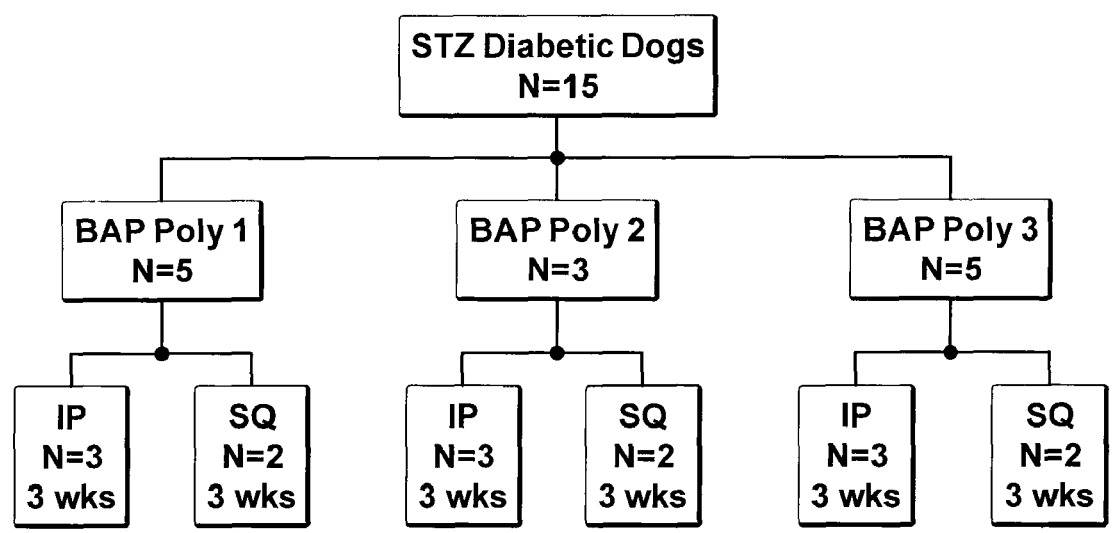
FIG. 3 is a graph showing a general experimental design for proving the efficacy of the present invention.
Figure 4A:
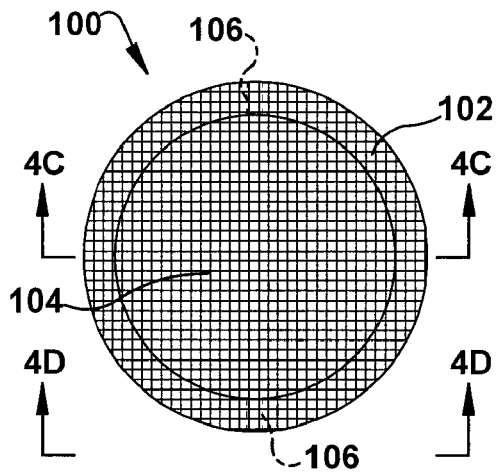
FIG. 4 is a drawing of one artificial pancreas embodiment of the present invention with 4(a) detailing a top view, 4(b) detailing a cutaway top view, 4(c) detailing a cutaway side view and 4(d) detailing a side view.
Figure 4B:
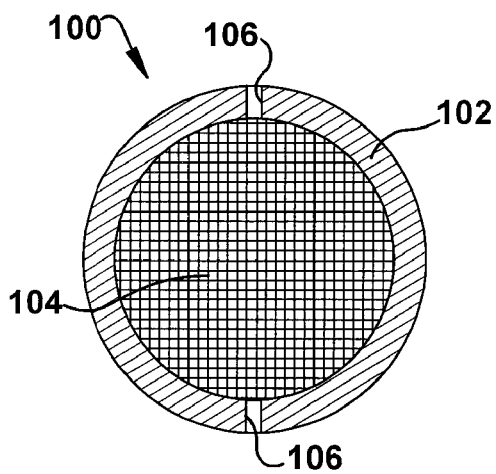
Figure 4C:
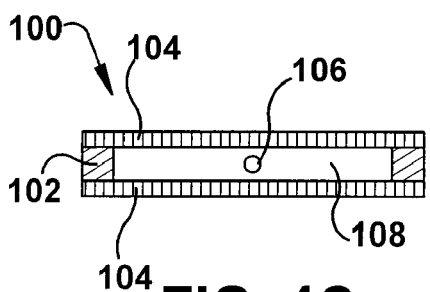
Figure 4D:
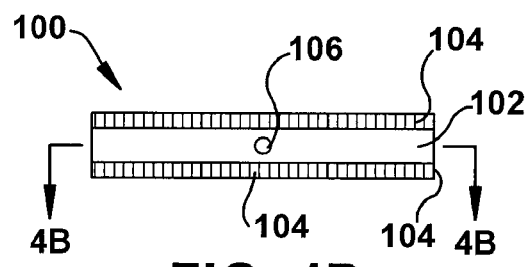

Two to four weeks after receiving STZ/ALX, the diabetes is treated with macroencapsulated porcine cells (12,000 islets per kg). Three different polymers are used to make BAP macroencapsulation devices. Each polymer is tested in 5 animals. For each group BAPs are implanted into an omental pouch in the peritoneum using a midline laparotomy incision under general anesthesia (see operative technique below) (N=3) or into a subcutaneous pocket created on the abdominal wall (N=2). No immunosuppression is used. Accucheck glucometers are used to monitor glucose levels daily prior to morning feeds for the first 5 days after chemotherapy and for the first five days after implantation. No exogenous insulin is administered beyond five days after implantation. An example of a research design is summarized in FIG. 3.

According to this example, all dogs undergo pre-operative and weekly post-operative serum C-peptide, IV glucose tolerance tests (IVGTT), insulin levels, as well as fasting blood sugars by glucometer every Monday, Wednesday, and Friday, to determine islet cell function in vivo. A complete blood count (CBC) is obtained weekly to assess inflammation. Liver function tests (i.e. alkaline phosphatase, alanine aminotransferase (ALT), and aspartate amhotransferase (AST)), renal function tests (blood urea nitrogen (BUN and creatinine (Cr)) are drawn before implantation and at three weeks to look for possible material toxicity. The BAPs are removed at 3 weeks, the dogs recover for 24 to 48 hrs, and the IVGTT and insulin levels are repeated prior to euthanizing the animals with intravenous BEuthansia-D (1 mL/5 kg).

In one example each group of five animals receive the devices either intraperitoneally (IP) into omental pouches (N=3) or subcutaneously (SQ) (N=2). The high $O_2$ permeability of the BAP membranes of the present invention make it feasible to use either site.

In one example a BAP is implanted in each of five STZ diabetic dogs and then in vivo pancreatic function (PF) tests are performed, which include IV glucose tolerance tests (IVGTT), serum insulin, and serum C-peptide. These tests are performed prior to implantation and weekly thereafter. The BAPs are removed at three weeks, and the animals are allowed to recover for one to three days. Pancreatic function (PF) is then retested to confirm that insulin and C-peptide secretion are coming from the BAP and not the native pancreas.

In a further example, the BAPs are recovered from the host and the contents thereof are tested for viable, functioning, islet cells. This can be done by immunostaining for insulin and glucagon, and preparing slides for light microscopy to assess islet morphology and granulation. Additionally, electron microscopy can be used to assess islet cell fine structure. A test for the absence of IgG within the BAP can also be conducted to show that immunochemicals from the host did not penetrate the BAP.

Exemplary Amphiphilic Networks for Use in the Present Invention

Various types of amphiphilic networks and/or co-networks can be used to form the amphiphilic membranes of the present invention. Some exemplary amphiphilic networks and/or co-networks are discussed below. However, it should be noted that the present invention is not limited to the following examples. Rather, any suitable amphiphilic network and/or co-network can be used in conjunction with the present invention so long as such networks and/or co-networks can provide a "support means" for living insulin producing cells.

In one embodiment, suitable amphiphilic networks and/or co-networks can be found in co-pending PCT Patent Application No. PCT/US2005/027163, filed Jul. 28, 2005 and entitled "Amphiphilic Co-Networks, Films Made From Amphiphilic Co-Networks and Uses for Such Co-Networks and Films," which is incorporated by reference herein in its entirety.

In one embodiment, the amphiphilic networks and/or co-networks used in conjunction with the insulin producing devices of the present invention are based upon amphiphilic copolymer networks or co-networks that are both hydrophobic and hydrophilic, where the copolymer networks and/or co-networks comprise polyalkylene glycol segments and disubstituted polysiloxane segments. In another embodiment, the amphiphilic networks and/or co-networks used in conjunction with the insulin producing devices of the present invention are synthesized using functional multiblock copolymers according to the formula $(AY)_x(BY)_y$, where A represents an alkylene glycol polymer having n repeating alkylene glycol units, B represents a disubstituted siloxane polymer having m repeating siloxane units, and Y represents a molecule (e.g., a silane) that functions both as a chain extender and a crosslinker.

In still another embodiment, the amphiphilic networks and/or co-networks used in conjunction with the insulin producing devices of the present invention comprise at least one hydrophilic segment and at least one hydrophobic segment. In one embodiment, the hydrophilic segments include at least one polyalkylene glycol (e.g., polyethylene glycol (PEG)) and the hydrophobic segments include at least one disubstituted polysiloxane (e.g., polydimethylsiloxane (PDMS)).

In one embodiment, the amphiphilic networks and/or co-networks used in conjunction with the insulin producing devices of the present invention are ideal (i.e., the lengths of each hydrophilic segments and the hydrophobic segments are identical). In another embodiment, the amphiphilic networks and/or co-networks used in conjunction with the insulin producing devices of the present invention do not have to be ideal. That is, if so desired, the hydrophilic segments and the hydrophobic segments can have different lengths.

Figure 5:
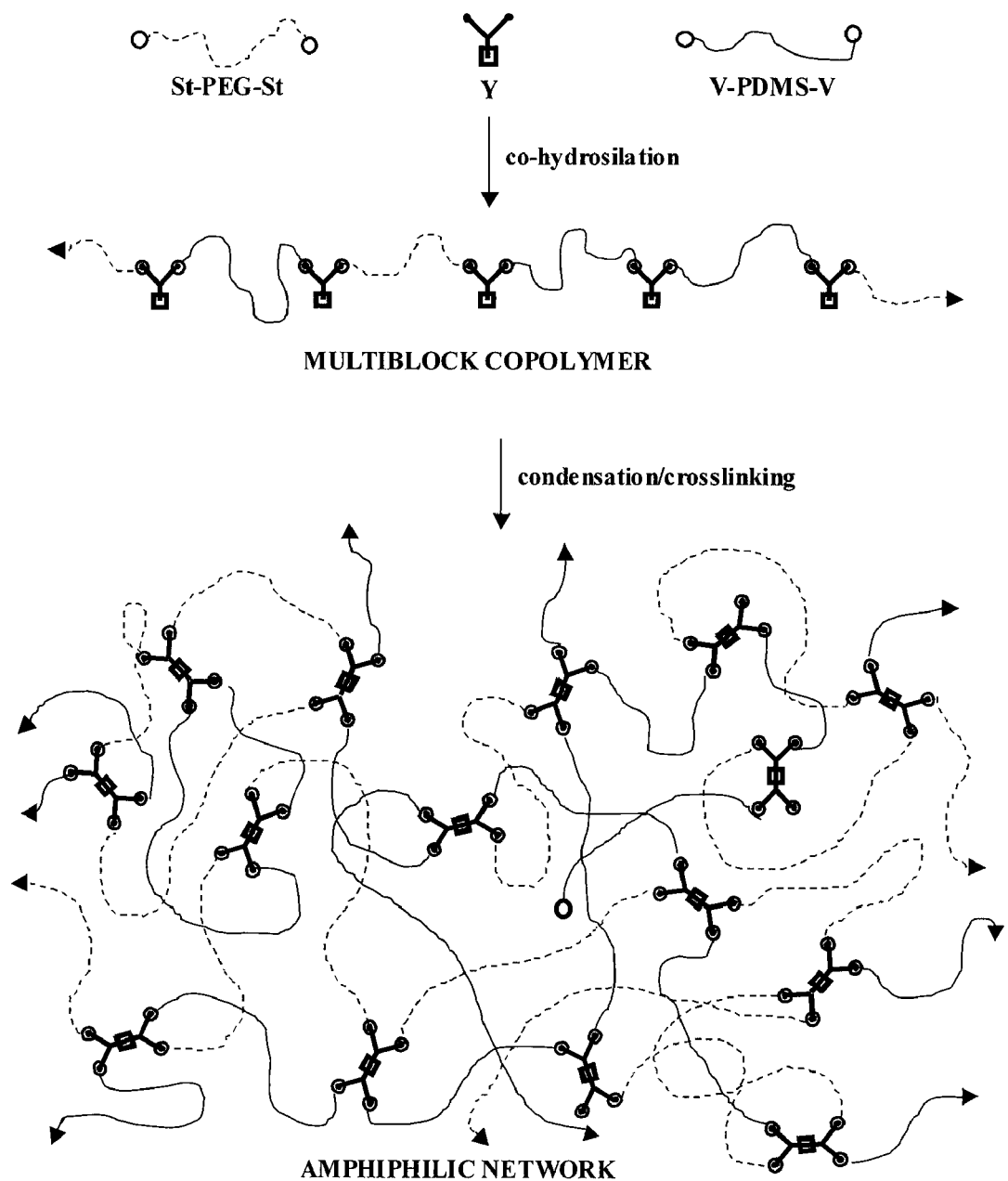
FIG. 5 illustrates a strategy for the synthesis of bi-continuous amphiphilic networks/co-networks in accordance with one embodiment of the present invention.

As is discussed above, the amphiphilic networks and/or co-networks used in conjunction with the insulin producing devices of the present invention are based upon amphiphilic networks that contain therein a molecule Y that acts as both a chain extender and a crosslinker. In one embodiment, Y is at least a tri-functional molecule. In another embodiment, Y is a tetra-functional molecule. As can be seen in FIG. 5, the bottom of the Y molecule binds to another Y molecule bottom during a crosslinking reaction to yield amphiphilic co-networks in accordance with the amphiphilic networks and/or co-networks used in conjunction with the insulin producing device. In one instance, during the crosslinking reaction two Y molecules combine to yield a tetra-functional crosslinking/chain extending molecule.

In one embodiment, Y is a tri-functional silane. Although not limited thereto, Y can be a silane according to the Formula (I) shown below.

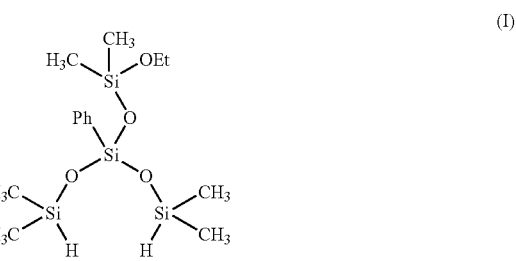

As would be apparent to one of ordinary skill in the art, Y is shown minus the polymer chains to which it binds. As will be explained below, Y binds to two polymer chains thereby acting as a chain extending agent. During the crosslinking reaction, two Y molecules link to form the aforementioned crosslinks and yield the following tetra-functional sub-molecule

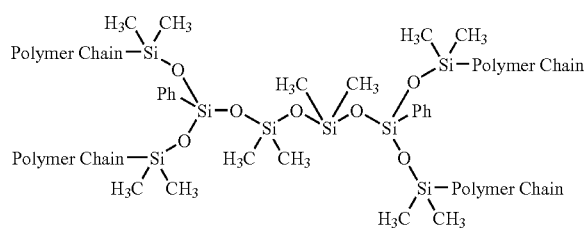

The words "Polymer Chain" denote bonds that are formed with a suitable hydrophilic polymer (denoted by A in the above-mentioned generic formula) or a suitable hydrophobic polymer (denoted by B in the above-mentioned generic formula). The chain extension bonds are formed via a one to one reaction between a terminal end of a polymer chain with each of the hydrogens in the silane according to Formula (I). The two chain extending Y molecules are then crosslinked via each Y molecule's ethoxy group to yield the above tetrafunctional chain extender/crosslinker.

It will be appreciated by those of ordinary skill in the art that the amphiphilic networks and/or co-networks used in conjunction with the insulin producing devices of the present invention can utilize other molecules that can function both as a chain extender and a crosslinker. All that is required for a compound to be used as molecule Y is that the compound fulfills at least the above two functions. First, the compound that is chosen to function as molecule Y must be able to extend the incompatible hydrophilic and hydrophobic polymers used to form the functional multiblock copolymers of the amphiphilic networks and/or co-networks used in conjunction with the insulin producing devices of the present invention according to the formula $(AY)_x(BY)_y$. Second, the compound that is chosen to function as molecule Y must be able to subsequently crosslink the polymer blocks of the multiblock copolymers according to the formula $(AY)_x(BY)_y$, thereby yielding an amphiphilic network/co-network.

As noted above, one problem associated with the synthesis of amphiphilic co-networks is how to overcome the thermodynamic incompatibility of the hydrophilic and hydrophobic constituents, and to unite two incompatible pre-polymers and/or polymers into a bi-continuous/bipercolating construct. Typically, crosslinking of such systems is carried out in homogeneous solution in a common good solvent at low pre-polymer and/or polymer concentrations, followed by the addition of a suitable crosslinker (i.e., by dissolving the two pre-polymers which are generally incompatible in their dry states). While this method yields uniform co-networks, the removal of the common solvent is accompanied by massive shrinkage, which renders the method technically impractical. Also, the dimensional stability of such co-networks is poor, the surface properties are hard to control, and the co-networks (or products formed therefrom) are fragile and difficult to manipulate. Among other things, the amphiphilic networks and/or co-networks used in conjunction with the insulin producing device overcome one or more of the above mentioned drawbacks.

The synthesis schemes of the amphiphilic networks and/or co-networks used in conjunction with the insulin producing device utilize one or more functional multiblock copolymers according to the formula $(AY)_x(BY)_y$, where A represents an alkylene glycol polymer having n repeating alkylene glycol units, B represents a disubstituted siloxane polymer having m repeating siloxane units, and Y represents a silane that functions both as a chain extender and a crosslinker. In one embodiment, the one or more functional multiblock copolymers according to the formula $(AY)_x(BY)_y$ are random multiblock copolymers. The one or more units of the functional multiblock copolymers according to the formula $(AY)_x(BY)_y$ are then crosslinked via two or more of the Y units by intermolecular condensation.

In one embodiment, the amphiphilic networks and/or co-networks used in conjunction with the insulin producing device initially involve preparing one or more random functional multiblock copolymers according to the formula $(AY)_x(BY)_y$, where A represents an alkylene glycol polymer having n repeating alkylene glycol units, B represents a disubstituted siloxane polymer having m repeating siloxane units, and Y represents a silane that functions both as a chain extender and a crosslinker. In one embodiment, the one or more random functional multiblock copolymers according to the formula $(AY)_x(BY)_y$ are prepared extending telechelic, for example, PEG and PDMS pre-polymers with a suitable chain extender/crosslinker Y. Subsequently, the one or more random functional multiblock copolymers are crosslinked via an acid catalyzed condensation reaction of the Y units. It should be noted, that although one possible crosslink strategy is disclosed herein, the amphiphilic networks and/or co-networks used in conjunction with the insulin producing device encompass other crosslinking strategies so long as the crosslinker functions as both a chain extending agent and a crosslinking agent.

Polymers:

As is discussed above, the amphiphilic copolymer networks or co-networks of the amphiphilic networks and/or co-networks used in conjunction with the insulin producing device contain at least one hydrophobic polymer and at least one hydrophilic constituent that have been bounded together by a suitable chain extending molecule. The chain extending molecule also functions as a crosslinking molecule during the formation of the amphiphilic networks and/or co-networks used in conjunction with the insulin producing device's amphiphilic networks/co-networks.

In one embodiment, the amphiphilic networks and/or co-networks used in conjunction with the insulin producing device utilize a combination of at least one polyalkylene glycol polymer with at least one disubstituted siloxane polymer. The at least one polyalkylene glycol polymer functions as the hydrophilic polymer, while the at least one disubstituted siloxane polymer functions as the hydrophobic polymer. As is noted above, the polymers are used to form the functional multiblock co-polymers according to the formula $(AY)_x(BY)_y$. Each polymer used to form the functional multiblock co-polymers according to the formula $(AY)_x(BY)_y$ independently contain from about 5 to about 5,000 repeating polymer units, or from about 10 to about 2,500 repeating polymer units, or from about 25 to about 1,000 repeating polymer units, or even from about 40 to about 500 repeating polymer units. Here, as well as elsewhere in the specification and claims, individual range limits may be combined.

It should be noted that the amphiphilic networks and/or co-networks used in conjunction with the insulin producing devices of the present invention are not limited to polymers having the above-mentioned number of repeating units. Instead, the amphiphilic networks and/or co-networks used in conjunction with the insulin producing devices of the present invention can utilize any suitable combination of hydrophilic and hydrophobic polymers having any number of repeating units so long as the polymers used can form functional multiblock co-polymers according to the formula $(AY)_x(BY)_y$. Another consideration that needs to be taken into account when choosing the polymers used to form the amphiphilic networks/co-networks of the amphiphilic networks and/or co-networks used in conjunction with the insulin producing devices of the present invention is the intended use for the amphiphilic network/co-network. As would be apparent to one of ordinary skill in the art, depending upon the desired use for the amphiphilic networks/co-networks used in conjunction with the insulin producing devices of the present invention, one may have to take into consideration a wide variety of physical, chemical and/or mechanical properties of the polymers used to form such networks.

In another embodiment, the amphiphilic networks and/or co-networks used in conjunction with the insulin producing device utilize a combination of at least one polyethylene glycol polymer with at least one polydimethylsiloxane polymer. Exemplary polyethylene glycol (styryl-ditelechelic polyethylene glycol (St-PEG-St)) and polydimethylsiloxane polymers (vinyl ditelechelic polydimethylsiloxane (V-PDMS-V)) are shown below in Formulas (II) and (III), respectively.

(II)

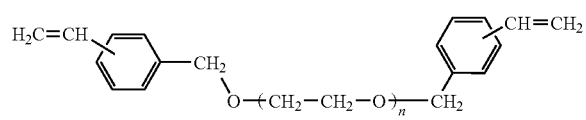

where n is equal to an integer in the range of about 5 to about 5,000, or from about 10 to about 2,500, or from about 25 to about 1,000, or even from about 40 to about 500, and (III)

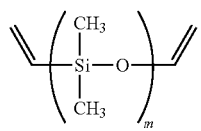

where m is equal to an integer in the range of about 5 to about 5,000, or from about 10 to about 2,500, or from about 25 to about 1,000, or even from about 40 to about 500. It should be noted that the amphiphilic networks and/or co-networks used in conjunction with the insulin producing device are not limited to just the polyethylene glycol and polydimethylsiloxane polymers of Formulas (II) and (III). Rather, in this embodiment any suitable combination of polyethylene glycol and polydimethylsiloxane polymers can be used.

The polydimethylsiloxane polymer of Formula (III) can, for example, be purchased from Gelest, Tulleytown, Pa. Alternatively, if so desired, the polymer of Formula (III) could be synthesized thereby permitting one to control the number of repeating units present in the polymer of Formula (III).

With regard to the polymer of Formula (II), this polymer can be synthesized by the reaction scheme shown below:

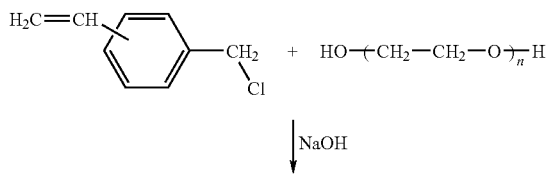

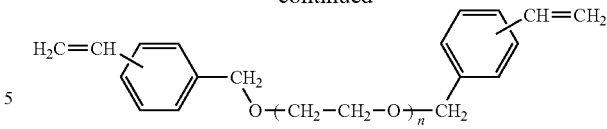

In one instance, 60 grams (0.0013 moles) of hydroxyl ditelechelic polyethylene glycol (HO-PEG-OH having a $M_n$ equal to 4600 grams/mole—available from Aldrich) and 0.032 grams (0.0001 moles) of tetrabutylammonium bromide (Aldrich) are dissolved in 60 grams of toluene (Fisher) at 50° C. Next, 7.8 grams (0.195 moles) of powdered NaOH (Fisher) is added to the above solution. Then, 19.9 grams (0.13 moles) of vinylbenzyl chloride (Aldrich) are added during vigorous stirring of the solution and the temperature is raised to 60° C. After three hours at 60° C. the solution is cooled to room temperature (approximately 25° C.) and 300 grams of methylene chloride (Fisher) is added thereto. The solution is then filtered and extracted with water. The methylene chloride is evaporated therefrom and the product is purified by repeated precipitations from methylene chloride into ether. The product is permitted to dry for one day in vacuum at room temperature and stored at −20° C. under a nitrogen atmosphere. The yield is 45 grams and the product is a faintly yellow powder.

Figure 6:
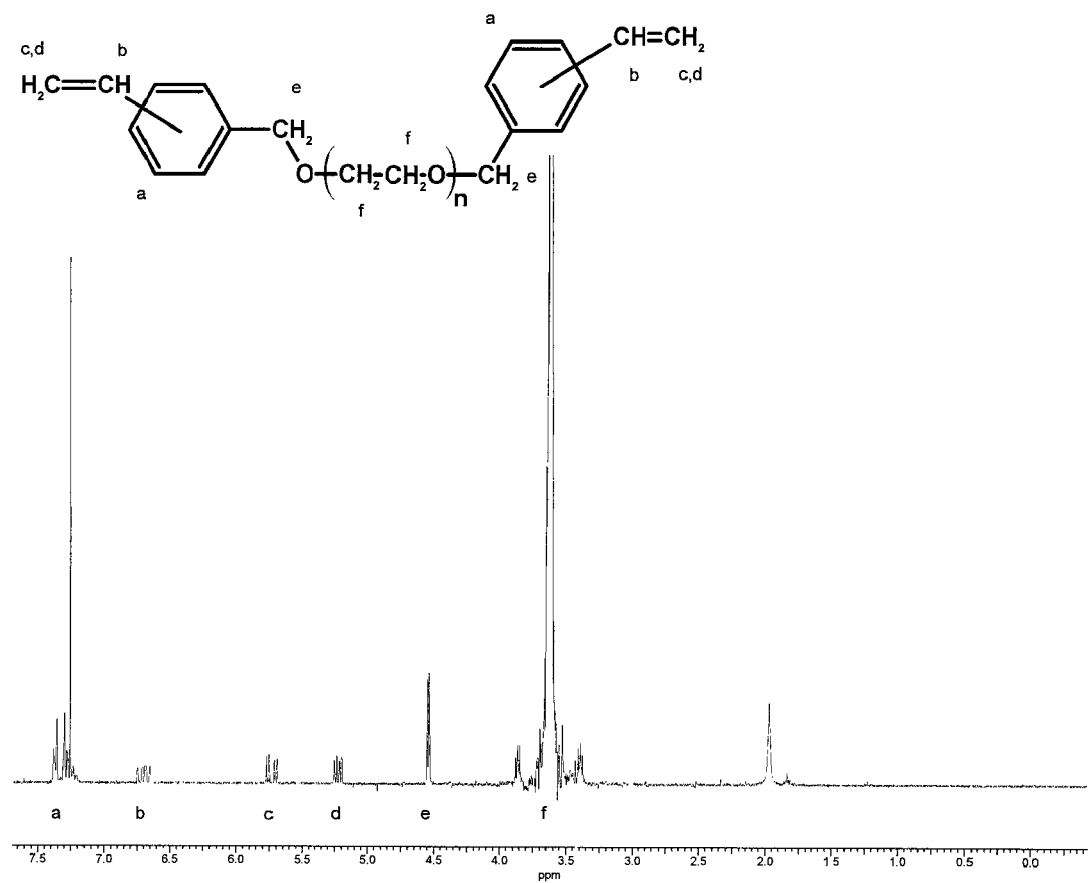
FIG. 6 is a $^1$H NMR spectrum of St-PEG-St.

The product produced by the above reaction is then subjected to $^1$H NMR spectroscopy using a Varian Unity 400-MHz spectrometer with $CDCl_3$ as the solvent in order to confirm that the product is in fact St-PEG-St. FIG. 6 shows the relevant spectra obtained from the $^1$H NMR spectroscopy.

In the above embodiment, styryl-ditelechelic PEG is chosen as the hydrophilic polymer over allyl-telechelic PEG in order to avoid the unwanted isomerization of $CH_2=CH-CH_2-$ end groups to $CH_3-CH=CH-$ during hydrosilation reaction that is used to form functional multiblock copolymers according to the formula $(AY)_x(BY)_y$. As is detailed above, this polymer can be readily obtained from inexpensive commercially available starting materials, i.e., HO-PEG-OH and vinylbenzyl chloride.

Figure 7:
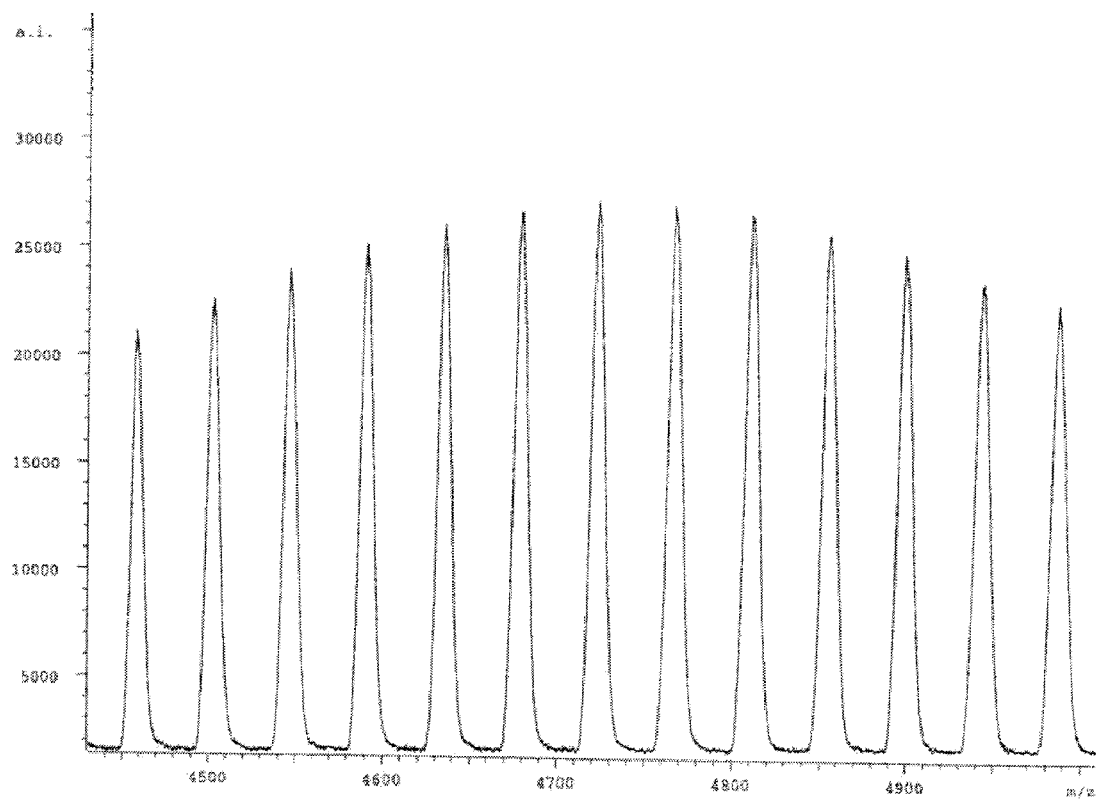
FIG. 7 is a MALDI-TOF spectrum of St-PEG-St.

FIG. 6 shows the NMR spectrum of St-PEG-St together with assignments. Integration of the protons associated with the $CH_2=CH-$ end groups relative to those of the backbone $CH_2$'s of PEG indicates close to quantitative functionalization. MALDI-TOF analysis (see FIG. 7) shows an absence of OH— end groups (or other chain ends), corroborating the conclusions reached by $^1$H NMR spectroscopy. FIG. 7 shows the center slice of the MALDI-TOF spectrum of St-PEG-St and indicates only peaks associated with different degrees of polymerization PEG carrying vinylbenzyl termini.

Chain Extender/Crosslinker

As is discussed above, the amphiphilic networks and/or co-networks used in conjunction with the insulin producing device utilize a molecule Y that acts as a chain extender that enables/facilitates the bonding of one polymer chain to another polymer chain. In one embodiment, the chain extender Y of the amphiphilic networks and/or co-networks used in conjunction with the insulin producing device enable/facilitate the bonding of at least one hydrophilic polymer chain to at least one hydrophobic polymer chain thereby yielding functional multiblock copolymers according to the formula $(AY)_x(BY)_y$.

Molecule Y also mediates the condensation/crosslinking of the multiblocks thereby yielding the desired amphiphilic networks/co-networks. Specifically, in one embodiment, the crosslinking function served by molecule Y can be accomplished by crosslinking to any one or more of another Y molecule in another functional multiblock copolymer chain, or to any suitable portion of the polymer chains contained in another functional multiblock copolymer chain. In one embodiment, the crosslinking function accomplished by Y is the result of a crosslinking bond formed between two Y molecules, each Y molecule being located in a separate functional multiblock copolymer chains As is discussed above, in one embodiment molecule Y can be any molecule that is at least a tri-functional molecule. In another embodiment, Y is a tetra-functional molecule. In one embodiment, Y is a tri-functional silane. Although not limited thereto, Y can be a silane according to the Formula (I) shown below:

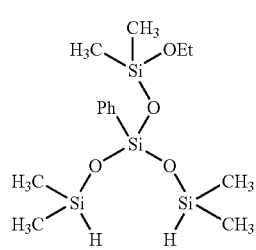
(I)

The compound according to Formula (I)—bis(dimethylsilyloxy) ethoxydimethylsilyloxy phenylsilane —(Ph)Si(OSi(CH$_3$)$_2$H)$_2$(OSi(CH$_3$)$_2$OEt)— is effective for the synthesis of an target amphiphilic network because (Ph)Si(OSi(CH$_3$)$_2$H)$_2$(OSi(CH$_3$)$_2$OEt) contains two Si—H groups to extend vinyl-telechelic polymers by cohydrosilation, and a Si-OEt group to condense two Y units to form a crosslink.

The central silicon Si atom in (Ph)Si(OSi(CH$_3$)$_2$H)$_2$(OSi(CH$_3$)$_2$OEt) is connected to three oxygens and can be more vulnerable to hydrolysis than the polymers used in the amphiphilic networks and/or co-networks used in conjunction with the insulin producing device. Accordingly, to increase the hydrolytic stability of this Si atom a phenyl substituted compound can be used.

The synthesis of (Ph)Si(OSi(CH$_3$)$_2$H)$_2$(OSi(CH$_3$)$_2$OEt) is carried out according to the reaction scheme shown below:

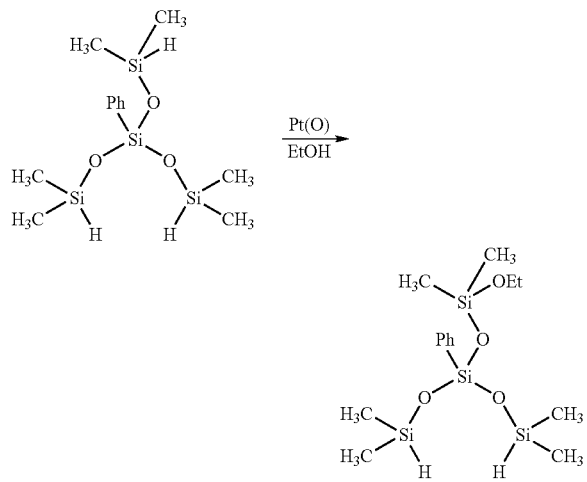

In a suitable flask 50 grams (0.152 moles) of tris(dimethylsiloxy) phenylsilane (available from Gelest, Tulleytown, Pa.) and 5 grams (0.111 moles) of anhydrous ethanol (Fisher) are mixed together. Fifty microliters (50 μL) increments of Karstedt's catalyst (a divinyldisiloxane complex—available from Gelest) are added to the solution after 10, 30 and 60 minutes of stirring. After two additional hours of stirring at room temperature, the mixture is vacuum distilled to remove the catalyst. Rectification on a spinning band column yields 19 grams of (Ph)Si(OSi(CH$_3$)$_2$H)$_2$(OSi(CH$_3$)$_2$OEt) (see Formula (I)), a colorless liquid having a purity greater than 98%, as confirmed by GC.

Generically, the compound according to Formula (I) can be synthesized by reacting tris(dimethylsilyloxy) phenylsilane with ethanol (EtOH) at a molar ratio of silane to alcohol of 1:0.333 in the presence of the Karstedt's catalyst. This reaction yields the target molecule (Formula (I)), plus di- and tri-OEt substituted by-products. The boiling points of these products are significantly different (approximately 10 to 15° C./OEt group), and the by-products can be easily separated by a spinning band column. Using the above techniques it is possible to consistently obtain high purity (greater than 97% as confirmed by GC) (Ph)Si(OSi(CH$_3$)$_2$H)$_2$(OSi(CH$_3$)$_2$OEt).

Figure 8:
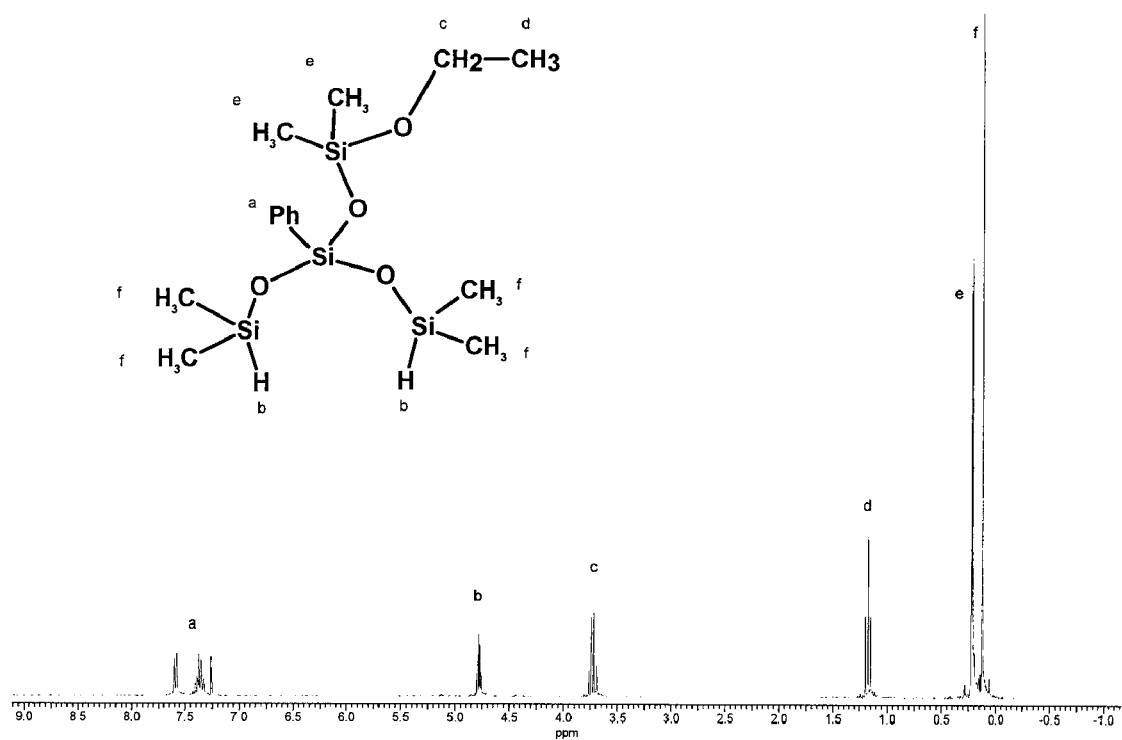
FIG. 8 is a $^1$H NMR spectrum of a chain extender/crosslinker according to one embodiment of the present invention.

FIG. 8 shows the $^1$H NMR spectrum of (Ph)Si(OSi(CH$_3$)$_2$H)$_2$(OSi(CH$_3$)$_2$OEt) and the key assignments. The spectrum confirms the expected structure. It should be noted that the use of the expensive spinning band column can be avoided by using acetic acid in place of ethanol in the above-mentioned reaction. The acetate substituent increases the boiling point differences between the mono-, di- and tri-substituted acetic acid reaction products to approximately 30 to 40° C./AcO group, and the target monoacetate can be obtained by simple vacuum distillation. The subsequent substitution of the AcO by EtO is a process known to those of ordinary skill in the art and a discussion herein is omitted for the sake of brevity. It should be noted however, that acetylation tends to yield small quantities of unidentified side products. Accordingly, in some circumstances it may be desirable to the EtOH synthesis route described above to yield the desired molecule Y for multiblock syntheses.

Functional Multiblock Copolymers:

As is discussed above, the amphiphilic networks or co-networks used in conjunction with the insulin producing device are synthesized using functional multiblock co-polymers according to the formula $(AY)_x(BY)_y$, where A represents an alkylene glycol polymer having n repeating alkylene glycol units, B represents a disubstituted siloxane polymer having m repeating siloxane units, and Y represents a molecule (e.g., a silane) that functions both as a chain extender and as a crosslinker.

As is noted above, one of the most important hurdles in the synthesis of amphiphilic co-networks is to overcome the massive macroscopic separation of the incompatible hydrophilic and hydrophobic polymer constituents. The amphiphilic networks and/or co-networks used in conjunction with the insulin producing device utilize the dual purpose chain extender/crosslinker Y to accomplish this task. In preparing functional multiblock copolymers according to the formula $(AY)_x(BY)_y$ (which as discussed above can be random functional multiblock copolymers), the first step is the coupling of two incompatible telechelic pre-polymers and/or polymers to create a functional multiblock copolymer by the use of a dual-purpose chain extender/crosslinker Y in a solvent that adequately dissolves the hydrophilic and hydrophobic polymers that are to comprise the basis of the amphiphilic co-network.

The functional multiblock co-polymers of the amphiphilic networks and/or co-networks used in conjunction with the insulin producing device can be synthesized from any suitable combination of at least one hydrophilic polymer and at least one hydrophobic polymer. In addition to the combination of hydrophilic and hydrophobic polymers, the synthesis reaction that yields the desired functional multiblock copolymers of the amphiphilic networks and/or co-networks used in conjunction with the insulin producing device also utilize a suitable chain extending/crosslinking molecule Y, as is discussed above in detail.

Although the amphiphilic networks and/or co-networks used in conjunction with the insulin producing device is not limited thereto, one such suitable set of reactants is St-PEG-ST (see Formula (II)), V-PDMS-V (see Formula (III)), and (Ph)Si(OSi(CH$_3$)$_2$H)$_2$(OSi(CH$_3$)$_2$OEt) (see Formula (I)). In this case St-PEG-St is molecule A and V-PDMS-V is molecule B in the generic formula (AY)$_x$(BY)$_y$. Using the synthesis method described below these three reactants yield a functional multiblock copolymer having the following formula:

conventional wet techniques because such blocks form stable micelles in solution. In contrast, the removal of starting A or B blocks from (AY)$_x$(BY)$_y$ multiblock copolymers of the amphiphilic networks and/or co-networks used in conjunction with the insulin producing device is easy by sequential extraction with differentiating solvents for the A and B blocks, respectively.

In the above example, the PEG and PDMS contaminants of (PEG-Y)$_x$(PDMS-Y)$_y$ can be easily removed by methanol and hexane extractions, respectively (i.e., by solvents in which the multiblock is insoluble).

Another significant advantage of the use of functional multiblock copolymers according to the generic formula (AY)$_x$(BY)$_y$ over end-functional di- or tri-blocks is in crosslinking. Crosslinking of (AY)$_x$(BY)$_y$ copolymers is efficient and rapid because it involves much less structural reorganization than end-linking of telechelic AB or ABA blocks.

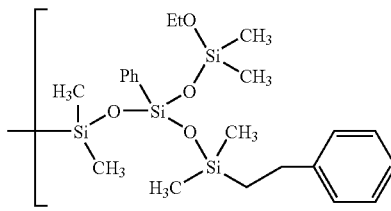

where n and m are independently equal to an integer in the range of about 5 to about 5,000, or from about 10 to about 2,500, or from about 25 to about 1,000, or even from about 40 to about 500, and x and y are independently equal to an integer in the to about 50,000, or from about 50 to about 25,000, or from about 100 to about 10,000, or from about 250 to about 5,000, or even from about 500 to about 1,000.

Due to the strict control of the stoichiometry of the reactants (see the discussion below), a random multiblock with controlled molecular weights can be obtained as a result of the amphiphilic networks and/or co-networks used in conjunction with the insulin producing device. The molecular weight of the multiblock copolymer can be controlled by the relative concentrations of the reaction partners (i.e., the chain extender Y in relation to the amount of polymers A and B). As is discussed above, Y is a dual-purpose chain extender/crosslinker. In one embodiment, Y is tri-functional, two functions of which are designed to extend the telechelic prepolymers and/or polymers to a random functional multiblock copolymer, while the third function (crosslinking) is inert during extension.

After chain extension is complete, the second step is to crosslink the functional multiblock copolymer via Y, thereby yielding an amphiphilic co-network.

The use of functional multiblock copolymers (AY)$_x$(BY)$_y$ for the synthesis of well-defined amphiphilic co-networks is fundamentally superior to syntheses of such co-networks by the use of end-functional di-blocks (e.g., Y-AB-Y) or tri-blocks (e.g., Y-ABA-Y). First of all, the removal of contaminating starting materials from the multiblocks copolymers of the amphiphilic networks and/or co-networks used in conjunction with the insulin producing device is far easier and more efficient than from di- or ti-blocks. Indeed, the separation of contaminating A or B blocks from AB di-blocks, or AB di-blocks from ABA tri-blocks is virtually impossible by While multiblocks self-aggregate into co-continuous morphologies over a broad composition range, di- or tri-blocks produce mostly lamellar or cylindrical morphologies which may not give co-continuous architectures upon crosslinking. Lastly, multiblocks do not contain gel, and, unlike branched amphiphilic blocks, are easily processible.

Co-networks formed by the crosslinking of well-defined multiblocks are; in most cases, ideal (i.e., the lengths of each hydrophilic and hydrophobic chain elements, respectively, are identical). In addition, such co-networks contain tetrafunctional crosslinkers as is shown in the generic formula below that represents a portion of a co-network and in FIG. 5.

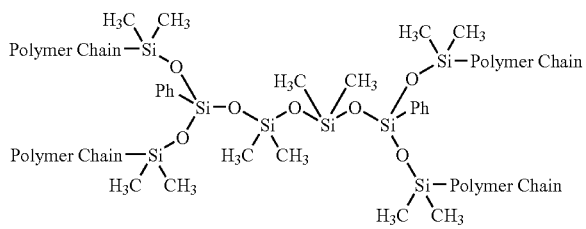

The words "Polymer Chain" denote bonds that are formed with a suitable hydrophilic polymer (denoted by A in the above-mentioned generic formula) or a suitable hydrophobic polymer (denoted by B in the above-mentioned generic formula). The chain extension bonds are formed via a one to one reaction between a terminal end of a polymer chain with each of the hydrogens in the silane according to Formula (I). The two chain extending Y molecules are then crosslinked via each Y molecule's ethoxy group to yield the above tetrafunctional chain extender/crosslinker. The fact that exactly four chains emanate from each crosslink site is desirable for narrow hydrophilic pore size distribution.

After a suitable combination of hydrophilic and hydrophobic polymers (e.g., St-PEG-St and V-PDMS-V) are reacted with a suitable chain extender/crosslinker Y (e.g., (Ph)Si(OSi(CH$_3$)$_2$H)$_2$(OSi(CH$_3$)$_2$OEt)) via a co-hydrosilation reaction to yield a functional multiblock copolymer according to the generic formula (AY)$_x$(BY)$_y$, the functional multiblock copolymer is then crosslinked, as is discussed above, by molecule Y via an acid catalyzed condensation reaction detailed below:

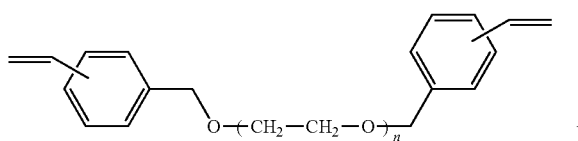 + 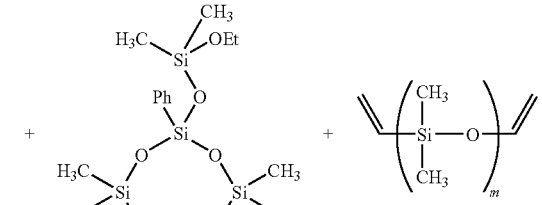 +

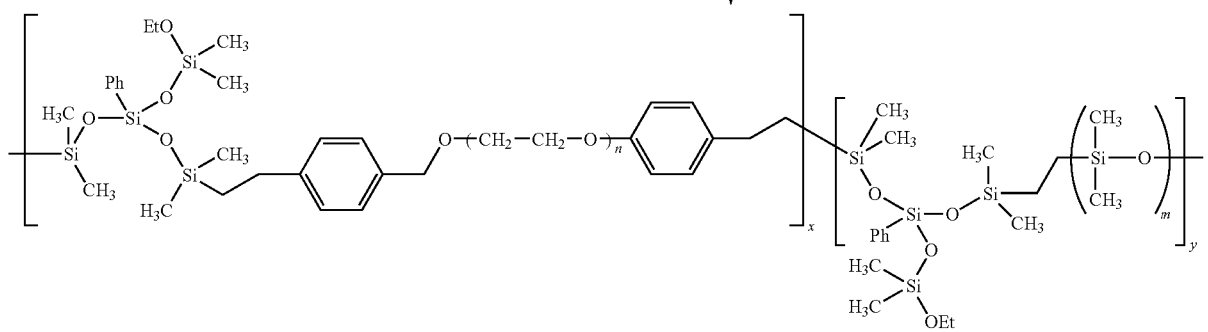

After extension, the above multiblock copolymer contains an ether linkage between the PEG and styryl moieties. This bond is inert during hydrosilation and subsequent crosslinking and it has the same or better overall chemical stability as PEG. Chain end modification did not affect the narrow molecular weight distribution of the starting HO-PEG-OH used to form the St-PEG-St. The molecular weight distribution of the PEG segment should be narrow to obtain membranes/co-networks with well-defined hydrophilic channel dimensions.

Exemplary Multiblock Copolymer Synthesis:

The multiblock copolymer, -(PEG-Y)$_x$-(PDMS-Y)$_y$—, shown in the above reaction immediately above is synthesized as follows, where Y is converted to structure (Ia) shown below in order to link the polymers and yield the desired multiblock copolymer

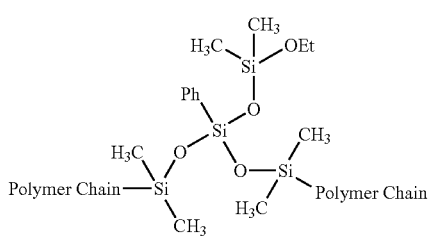

(Ia)

where the words "Polymer Chain" denote the fact that at least one hydrophilic polymer chain and/or at least one hydrophobic polymer chain are bonded to structure (Ia).

Eight grams (1.67 mmol) of St-PEG-St and 8.7 grams (1.45 mmol) of V-PDMS-V are dissolved in 160 grams of toluene. Next, 2 grams of powdered CaH$_2$ is added to the mixture. The solution is stirred for one hour, filtered under N$_2$ and 1.25 grams (3.81 mmol) of (Ph)Si(OSi(CH$_3$)$_2$H)$_2$(OSi(CH$_3$)$_2$OEt) is added. Hydrosilation is initiated by the addition of 290 ml of Karstedt's catalyst and allowed to proceed for three hours at 60° C. The reaction product is permitted to cool for an hour, and then the toluene solvent is evaporated and the product is dried under vacuum. The copolymer product is extracted by 2×500 mL hexane, dried in vacuum, extracted by 3×800 mL methanol, and dried in vacuum. The yield is 12.2 grams. The multiblock copolymer is a slightly yellow rubbery material.

Toluene is used as the solvent in which the reaction is carried out because it is inert with respect the polymer charges used to produce the desired multiblock copolymer. The charges should be dry to prevent the oxidation of —SiH groups to —SiOH groups (i.e., premature crosslinking), and/or the formation of too low molecular weight (M$_w$) products, and their slow condensation. Thus, the polymer charges can be dried with CaH$_2$ to reduce/eliminate the chance that premature crosslinking occurs.

Statistics dictate that despite the unequal reactivities of the St and V end groups toward hydrosilation by (Ph)Si(OSi(CH$_3$)$_2$H)$_2$(OSi(CH$_3$)$_2$OEt) (the vinylsilyl group is much more reactive than the styryl group), random multiblock copolymers will arise because of the stoichiometry used:

St-PEG-St/(Ph)Si(OSi(CH$_3$)$_2$H)$_2$(OSi(CH$_3$)$_2$OEt)N-PDMS-V=$x$/=2($x$+$y$)/$y$ where x and y are the concentrations of the two polymers, respectively. Due to this stoichiometry, the first product that must arise is (Ph)Si(OSi(CH$_3$)$_2$H)(OSi(CH$_3$)$_2$OEt)-PDMS-(Ph)Si(OSi(CH$_3$)$_2$H)(OSi(CH$_3$)$_2$OEt)- because one of the SiH functions in (Ph)Si(OSI(CH$_3$)$_2$H)$_2$(OSi(CH$_3$)$_2$OEt) is preferentially consumed by the vinyl termini of V-PDMS-V; negligible amounts of (Ph)Si(OSi(CH$_3$)$_2$H)(OSi(CH$_3$)$_2$OEt)-PEG-St may also form.

During the first phase of the reaction, the concentrations of V-PDMS-V and (Ph)Si(OSi(CH$_3$)$_2$H)$_2$(OSi(CH$_3$)$_2$OEt)

gradually diminish, while that of St-PEG-St remains essentially unchanged. During the second phase the hydrosilation of St-PEG-St starts, however, at this point essentially all V-PDMS-V is consumed. At this stage the —SiH groups that remain to react with St-PEG~St are mainly those attached to PDMS, i.e., -PDMS-Si(Ph)(OSi(CH$_3$)$_2$H)(OSi(CH$_3$)$_2$OEt). In this sense St-PEG-St is a chain extender of Si(Ph)(OSi(CH$_3$)$_2$H)(OSi(CH$_3$)$_2$OEt)-PDMS-Si(Ph)(OSi(CH$_3$)$_2$H)(OSi(CH$_3$)$_2$OEt) (or larger Si(Ph)(OSi(CH$_3$)$_2$H)(OSi(CH$_3$)$_2$OEt)-telechelic PDMS blocks). Due to this concentration drift, co-hydrosilation will be random and therefore random multiblock according to the formula $(AY)_x(BY)_y$ will form.

Since chain extension is akin to polycondensation, the molecular weights are a function of the stoichiometry of the reactants (i.e., r=[Y]/[polymers]). Chain extension will be inefficient if the concentration of the vinyl groups or Y is in excess—that is if r is greater than 1.4 or less than 1.0. The molecular weight of the multiblock copolymers will be low and they will be contaminated by the polymers starting materials. In the r equal to 1.4 to 1.0 range, the $M_n$ of the multiblock copolymers is controlled by r. In one embodiment, the $M_n$ range is about 30 to about 100 kg/mol (the degree of polymerization—$DP_n$ is in the range of about 6 to about 20). If the $M_n$ is less than about 30 kg/mol, significant amounts of di- or tri-blocks will form and crosslinking will be inefficient because these low $M_w$, species contain 1 to 4 SiOEt groups (depending on the type of chain ends)—not all of which may form crosslinks. If the $M_n$ is greater than about 100 kg/mol, multiblock copolymer processing will be cumbersome (high viscosity solutions and melts, residual stresses, etc will occur).

The nature of the terminus (Silt St, or V), can be controlled by the use of a slight excess of Y or the polymer charges. When a slight excess of Y is used, the excess Y yields SiH terminated multiblocks rather than vinyl termini. While vinyl groups do not react with the SiOEt group of Y, SiH (or SiOH) may do so, which results in more efficient crosslinking of low M—multiblocks ($DP_n$=2 to 3), which do not contain multiple SiOEt functionalities. The multiblocks with SiH termini should be stored under vacuum to avoid the oxidation of SiH to SiOH groups (i.e., premature crosslinking).

copy. Finally, columns seven and eight give molecular weight data obtained by GPC (with polystyrene calibration).

It should be noted that here, as well as elsewhere in the specification, number-average molecular weights ($M_n$'s), weight-average molecular weights ($M_w$'s), and molecular weight distributions (MWD) ($M_w/M_n$) are obtained with a Waters GPC instrument equipped with a series of six Styragel columns (HR 0.5, HR 1, HR 3, HR 4, HR 5 and HR 6; Waters) calibrated with narrow-MWD polystyrene standards, a refractive-index (RI) detector (Optilab, Wyatt Technology), a dual-ultraviolet absorbance detector (Waters 2487), and a laser light scattering detector (Mimidawn, Wyatt Technology). The flow rate was 1 mL of THF/min.

Figure 9A:
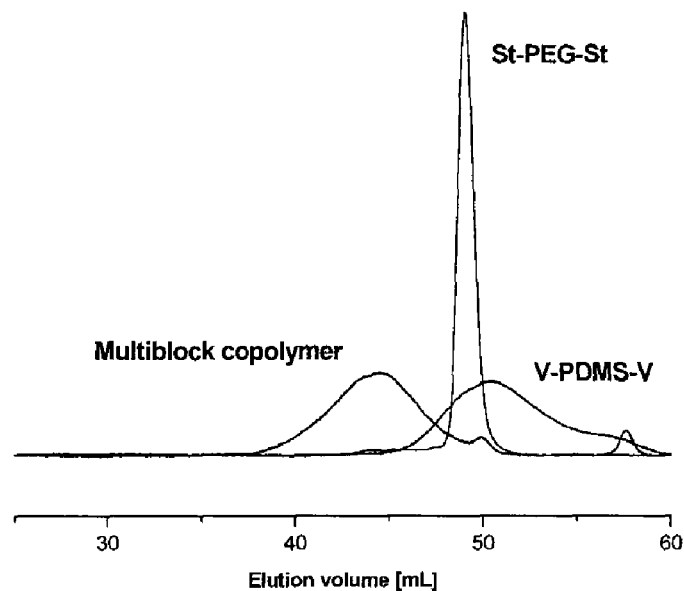
FIG. 9a is a GPC-RI trace of the polymer charge materials and the MBC-42 (see Table 1 below)

FIG. 9a shows the GPC-RI traces of the starting materials and the multiblock copolymer product MBC-42. The refractive index increments (dn/dc) in THF of both polymer charges are low, however, the value for PDMS is much smaller than that of PEG (dn/dc$_{PEG}$=0.46, dn/dc$_{PDMS}$<0.1). Thus the refractive index (RI) trace of the multiblock shows mainly the PEG constituent, while the PDMS segments are almost invisible. The product exhibits a relatively broad molecular weight distribution, typical of polymers made by polycondensation. High molecular weight contaminants are absent (no peaks or tails at low elution volumes) indicating that the —SiOEt groups were stable during synthesis and premature crosslinking did not occur. The small hump at 51 mL is due to unreacted PEG; a small amount of PDMS must also be present; however, it is invisible because of its very low dn/dc value.

Since the multiblock copolymers of the Table 1 are insoluble and do not form micelles in hydrophilic or hydrophobic solvents, contamination from the polymer charges or from homopolymers can be readily removed by precipitation or extraction. The V-PDMS-V can be removed by hexane extractions (see column 4, Table 1) and the St-PEG-St (and/or homo-PEG blocks) can be removed by repeated extractions with methanol (column 5, Table 1). Those of skill in the art will recognize that there are other suitable methods by which to remove contaminants from the multiblock copolymers of the amphiphilic networks and/or co-networks used in conjunction with the insulin producing device. Accordingly, the amphiphilic networks and/or co-networks used in conjunc-

TABLE 1

| Multiblock Copolymer | Charge Compositions | | Extractables | | Composition and Mn of Extracted Multiblocks | | |
|---|---|---|---|---|---|---|---|
| | PEG$_{4.6k}$/Y/PDMS$_{6k}$ g/g % | Y/Polymers (r) mol/mol | Hexane Soluble g/g % | Methanol Soluble g/g % | PEG Content$^a$ g/g % | $M_n^b$ kg/mol | $M_n/M_w$ |
| MBC-17 | 20/7/73 | 1.2 | 28 | 10 | 17 | 56 | 2.4 |
| MBC-42 | 45/7/48 | 1.15 | 8 | 22 | 42 | 72 | 2.9 |

$^a$by $^1$H NMR
$^b$by GPC

Table 1 summarizes multiblock copolymers made in accordance with the amphiphilic networks and/or co-networks used in conjunction with the insulin producing device and some of their characteristics. Column one gives abbreviations (MBC=multiblock copolymer) with the digits specifying the percent PEG in the purified MBC. Columns two and three show the relative amounts of polymers and Y in the charges used to form each multiblock copolymer, and r, respectively. Columns four and five give the results of multiblock copolymer extractions in terms of percent hexane and methanol soluble fractions. Column six shows the PEG content of the multiblock copolymers determined by $^1$H NMR spectrostion with the insulin producing device are not limited to just the extraction methods discussed above.

Extraction with methanol removes PEG quantitatively together with some low $M_w$ multiblocks. The relatively high methanol and hexane soluble fractions of MBC-42 and MBC-17 may be due to the broad molecular weight distribution of V-PDMS-V. Low $M_w$, multiblock copolymers ($DP_n$=2 to 5) and multiblock copolymers with higher than average PEG contents may be soluble in methanol, and, similarly, higher than average PDMS content multiblock copolymers may be soluble in hexane.

Figure 9B:
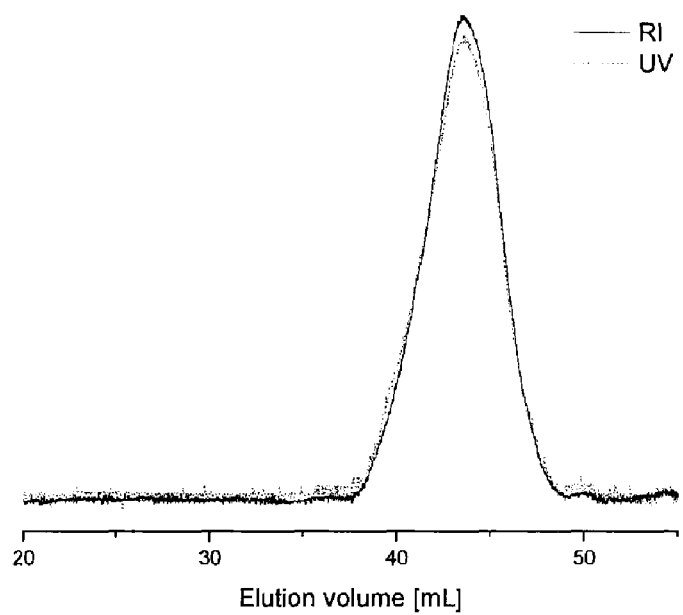
FIG. 9b is a GPC-UV and RI signal trace of MBC-42.

FIG. 9b shows the GPC-RI and -UV signals of MBC-42 after sequential extraction with hexane and methanol. Both polymers charges and low $M_w$ multiblock copolymers are absent. The UV adsorption is due to the terminal phenyl groups in St-PEG-St and to the phenyl substituent in the chain extender/crosslinker Y. The RI signal shows only the PEG component ($dn/dc_{PDMS}$ is less than 10% of $dn/dc_{PEG}$), whereas the UV signal is proportional to the PEG plus the chain extender/crosslinker Y. Thus a comparison of these signals gives the ratio of these moieties as a function of molecular weight ($M_w$). Since the UV and RI traces are essentially identical, the composition of the multiblock copolymers is independent of molecular weight (i.e., extension to multiblock copolymers is random).

The $M_n$'s of MBC-17 and MBC-42 were 56 and 72 kg/mol, respectively (i.e., $DP_n=10$ to 15). The multiple extractions slightly decrease the PEG content of the multiblock copolymers (see the charge and product compositions in Table 1). The PEG content decreases because hydrosilation of the styryl end groups is less efficient than that of the vinylsilyl groups, and because the PEG contents were calculated from $^1$H NMR spectra and the styryl end groups do not contribute to the PEG content of the multiblock copolymers.

Figure 10:
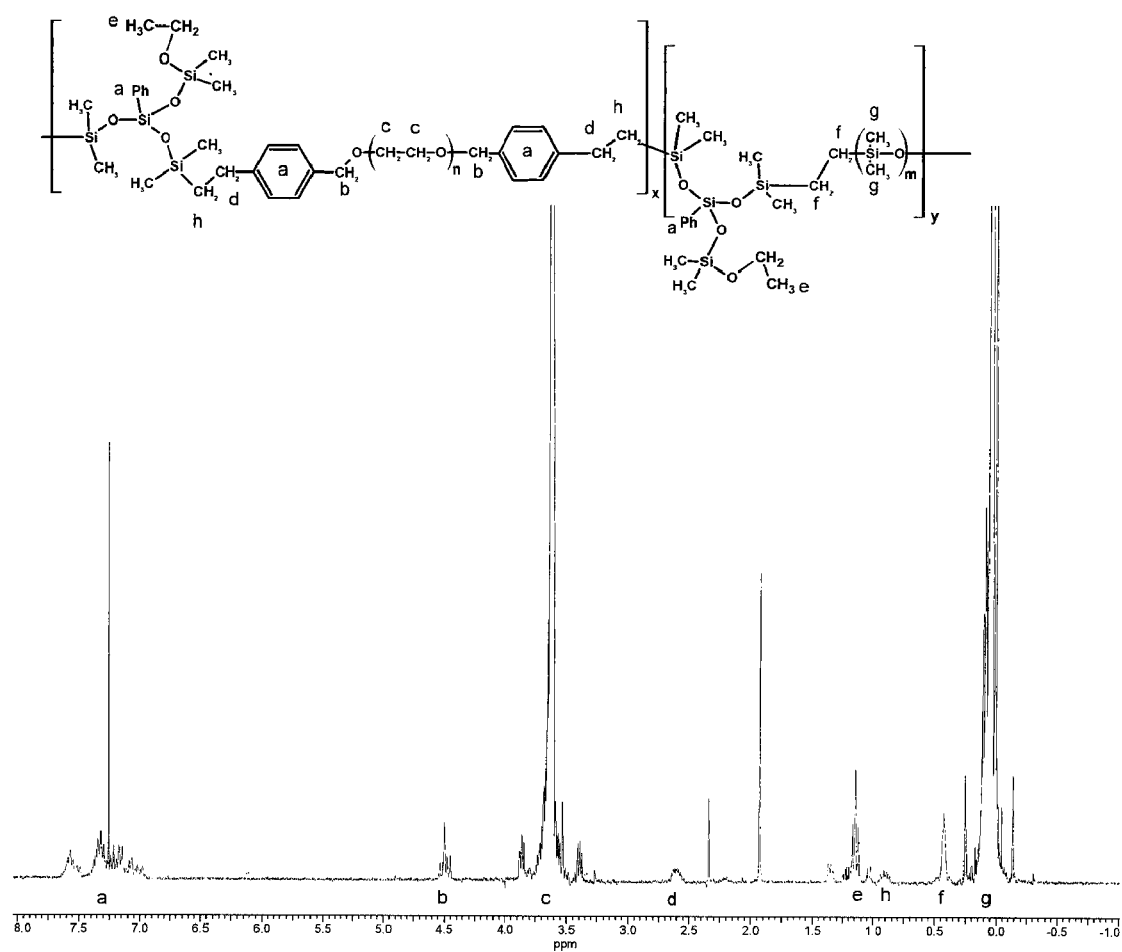
FIG. 10 is a $^1$H NMR spectrum of a multiblock copolymer according to one embodiment of the present invention (MBC-42 from Table 1 below)

FIG. 10 shows the $^1$H NMR spectrum of a representative multiblock copolymer together with assignments. As can be seen from the spectra of FIG. 10, the spectra illustrate the absence of vinylsilyl and styryl end groups, which in turn indicates essentially quantitative extension. Although a slight excess of $(Ph)Si(OSi(CH_3)_2H)_2(OSi(CH_3)_2OEt)$ is used in the examples of Table 1 (see Column 3), the SiH groups are invisible due to their very low concentration. The spectrum shows the expected resonances of the hydrosilated segments.

In one embodiment, the multiblock copolymers form optically transparent membranes. Optical clarity is evidence for the absence of macroscopic phase separation, and suggests that the dimensions of the incompatible PEG and PDMS domains are well below the wavelength of visible light.

Figure 11:
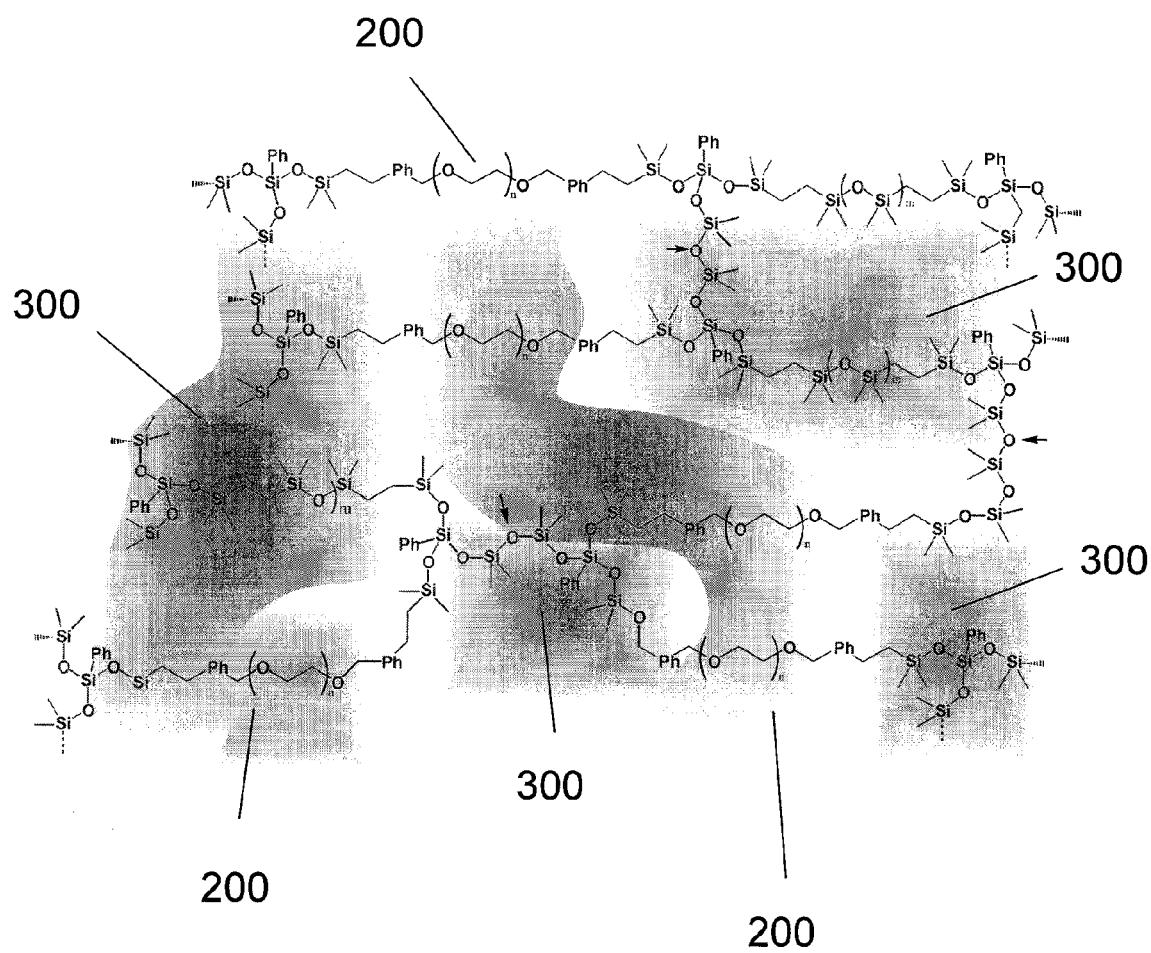
FIG. 11 is an illustration of an idealized structure of an amphiphilic co-network formed in accordance with one embodiment of the present invention in which the tetra-functional crosslinks are emphasized, the arrows indicate the newly formed oxygen bridges; the  indicate continuing polymer segments; and the dashed lines indicate continuing crosslinks.

Amphiphilic Co-Networks:

The final step to obtain the co-networks of the amphiphilic networks and/or co-networks used in conjunction with the insulin producing devices of the present invention is to subject a suitable multiblock copolymer to crosslinking. In the amphiphilic networks and/or co-networks used in conjunction with the insulin producing devices of the present invention, crosslinking is accomplished via condensation of the pendant SiOEt groups and the formation of intermolecular —SiOSi— bridges. FIG. 11 illustrates an idealized structure of an amphiphilic co-network formed in accordance with one embodiment of the amphiphilic networks and/or co-networks used in conjunction with an insulin producing device of the present invention. In FIG. 11, the domains labeled with reference numeral 200 are co-continuous hydrophilic domains, and the domains labeled with reference numeral 300 are co-continuous hydrophobic domains.

Crosslinking of the multiblock copolymers of the amphiphilic networks and/or co-networks used in conjunction with the insulin producing devices of the present invention are effected by condensation via addition of an acid miscible with the multiblock copolymer in a toluene solution. In one embodiment, the amphiphilic networks and/or co-networks used in conjunction with the insulin producing devices of the present invention utilize an alkylbenzene sulfonic acid. It should be noted that the amphiphilic networks and/or co-networks used in conjunction with the insulin producing devices of the present invention are not limited to solely the acid listed above. Those of ordinary skill in the art will recognize that other acids can be used to effect crosslinking of the multiblock copolymers formed in accordance with the with the insulin producing devices of the present invention.

Alkylbenzene sulfonic acid performs satisfactorily at room temperature or, can be made to perform better at 60° C. in the presence of moisture to enhance the rate of crosslinking. Since the solubility of sulfonic acids and their salts in the siloxane phase is low, a benzene sulfonic acid with a long ($C_{11-13}$) alkyl substituent is utilized. This ensures good solubility in the PDMS phase. Crosslinking can be more efficient by the use of an acid partially neutralized with an amine. Accordingly, in one embodiment, a mixture of sulfonic acid/pyridinium sulfonate (50/50 mol/mol %) is used as a catalyst. The multiblock copolymers of the amphiphilic networks and/or co-networks used in conjunction with the insulin producing device are highly viscous liquids even above the melting point of PEG segments (approximately 50° C.). Therefore, polymer membranes are prepared, as detailed below, by casting multiblock copolymers dissolved in toluene via the use of glass molds at 60° C. The solvent rapidly evaporates and crosslinking is complete within approximately 3 hours.

Amphiphilic co-networks in accordance with the amphiphilic networks and/or co-networks used in conjunction with the insulin producing devices of the present invention are prepared by: (1) crosslinking well-defined $(AY)_x(BY)_y$ multiblock copolymers (see APCN-16 and APCN-40 in Table 2 below), and (2) by crosslinking mixtures of different compositions of multiblock copolymers (see APCN-24 and APCN-32 in Table 2 below).

TABLE 2

| Amphiphilic Co-Network | Multiblock Copolymer Charges | | THF Extractable g/g % | PEG Content of Extracted Networks[a] g/g % |
|---|---|---|---|---|
| | MBC-17 % | MBC-42 % | | |
| APCN-16 | 100 | — | 2.6 | 16 |
| APCN-24 | 66 | 33 | 2.3 | 24 |
| APCN-32 | 33 | 66 | 3.8 | 32 |
| APCN-40 | — | 100 | 4.2 | 40 |

[a]calculated from the PEG content of polymers charged and taking in consideration the PEG content of the extract (determined by $^1$H NMR)

Column 1 gives co-network abbreviations (APCN=amphiphilic co-network) with the digits indicating the percent PEG in the APCNs. Columns 2 and 3 give the compositions of the charges prepared with the two MBCs specified in Table 1. The membranes are exhaustively extracted with THF and Column 4 shows the THF soluble fractions. The low amounts of THF solubles (less than 4.2%) indicate efficient crosslinking. The last column in Table 2 gives the PEG content of the membranes, calculated from the PEG contents on the charge, taking in consideration the PEG content of the THF soluble fraction (the latter determined by $^1$H NMR spectroscopy). The PEG content in the THF extract is generally a little higher than that of the charge. This results in a small decrease in the PEG content of the membrane. Alkyl sulfonate catalyst residues are also removed by extraction with THF. The final membranes are smooth and optically clear, optical clarity is construed as evidence for the absence of macroscopic phase separation of the PEG and PDMS segments.

Specifically, the synthesis of the amphiphilic co-networks detailed in Table 2 are accomplished as follows. Five one gram increments of each multiblock copolymer charge detailed in Table 2 are each dissolved in 10 mL of toluene. Given that there are four different multiblock copolymer combinations this yields a total of 20 samples. Each multiblock copolymer solution contains 0.0002 moles of SiOEt groups. Next, 3.2 mg of alkylbenzene sulfonic acid (available from Alfa Aesar) and 0.3 mg pyridine are added to each of the 20 solutions. The solutions are then poured into individual glass molds. The molds each have a diameter of 6 cm. All of the molds are then heated in an oven at 60° C. until the toluene evaporates (approximately 30 minutes). The remaining samples in each mold are then heated for 3 more hours at 60° C., removed from their respective molds, dried in vacuum and extracted with tetrahydrofuran until weight constancy. The co-networks produced by the above process are transparent rubbery sheets.

In light of the above, the amphiphilic networks and/or co-networks used in conjunction with the insulin producing device permit, among other things, the synthesis of nearly ideal tetra-functional amphiphilic co-networks consisting of PEG and PDMS segments. The synthesis can be achieved by using a dual-purpose chain extender/crosslinker—(Ph)Si(OSi(CH$_3$)$_2$H)$_2$(OSi(CH$_3$)$_2$OEt) (see Formula (I))—whose first function is to extend the incompatible PEG and PDMS polymers into functional multiblock copolymers according to the formula $(AY)_x(BY)_y$, and subsequently crosslink the multiblock copolymers by condensing the SiOEt functions into —Si—O—Si— bridges. As detailed above, in one embodiment, the amphiphilic networks and/or co-networks used in conjunction with the insulin producing device relate to amphiphilic co-networks formed from multiblock copolymers of with the following structure -(PEG-(Ph)Si(OSi(CH$_3$)$_2$ H)$_2$(OSi(CH$_3$)$_2$OEt)-PDMS-(Ph)Si(OSi(CH$_3$)$_2$H)$_2$(OSi(CH$_3$)$_2$OEt))$_n$.

Swelling Characteristics of the Amohiphilic Co-Networks:

The equilibrium swelling characteristics of various amphiphilic co-networks made in accordance with the amphiphilic networks and/or co-networks used in conjunction with the insulin producing devices of the present invention are determined at room temperature. Suitable pre-weighed co-network samples (approximately 20×20×0.4 mm) are placed in distilled water, and periodically gently shaken. The extent of swelling is determined periodically by removing the membranes from the solvent, removing the water adsorbed to the surfaces by blotting with tissue paper, and weighing the membranes. Equilibrium swelling is recorded when the weight of the water-swollen membranes do not change for 24 hours in the solvent (water). The swelling of co-networks in water is obtained by the following formula:

$$S_{H_2O}=100(m_{sw,H_2O}-m_d)/m_d.$$

where $m_{sw,H_2O}$ and $m_d$ are the masses of water-swollen and dry co-networks, respectively.

The above procedure is used to determine the swelling of the same co-networks in n-heptane. The swelling of co-networks in n-heptane is obtained by the following formula:

$$S_{C_7}=100(m_{sw,C_7}-m_d)/m_d$$

where $m_{sw,C_7}$ is the mass of n-heptane-swollen membrane.

The swelling of PEG domains in water, and that of PDMS domains in n-heptane is expressed by the following formulas:

$$S_{H_2O,PEG}=100(m_{sw,H_2O}-m_d)/M_{PEG}$$

and $$S_{C_7,PDMS}=100(m_{sw,C_7}-m_d)/m_{PDMS}$$

where $m_{PEG}$ and $m_{PDMS}$ are the masses of the PEG and PDMS domains in the co-networks, respectively.

Figure 12:
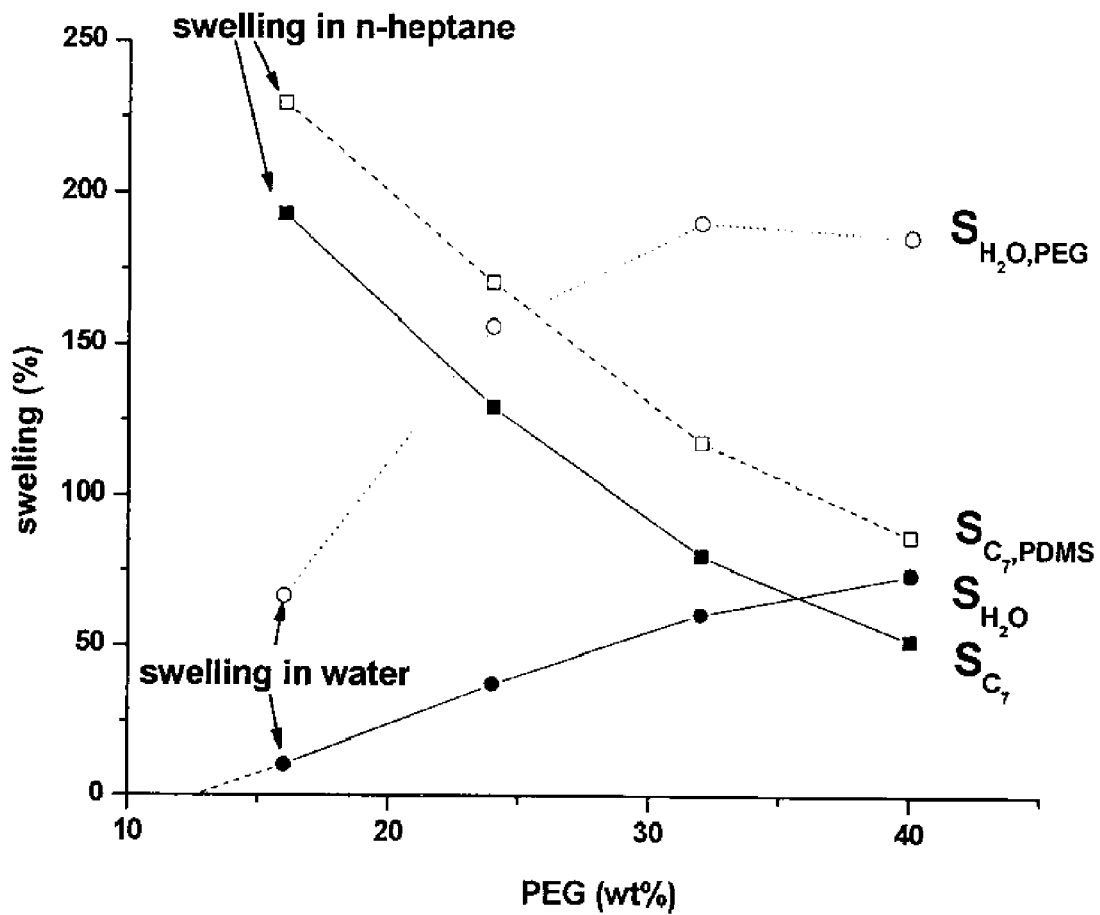
FIG. 12 is an illustration of the swelling behavior of PEG/PDMS amphiphilic co-networks in water and n-heptane. $S_{H_2O}$ and $S_{C_7}$ are swelling ratios relative to the dry mass of the co-networks, $S_{H_2O,PEG}$ and $S_{C_7,PDMS}$ are swelling ratios of the swollen PEG and PDMS phases relative to the dry masses of PEG and PDMS.

FIG. 12 shows the swelling behavior of various composition co-networks in water and n-heptane, $S_{H_2O}$ and $S_{C_7}$, and the swelling of PEG domains in water and PDMS domains in n-heptane, $S_{H_2O,PEG}$ and $S_{C_7,PDMS}$, as a function of PEG content (the PEG content corresponds to the number given in column 1 of Table 2). The swelling in water increases with increasing PEG content. Conversely, the swelling decreases in n-heptane with increasing PEG content. The swelling in water can be smoothly back-extrapolated to approximately 13% PEG, suggesting that water starts to percolate at this PEG content. The fact that both water and n-heptane swell these co-networks indicates bi-continuous/bipercolating architecture of incompatible PEG and PDMS phases.

Inspection of the swelling behavior of the individual domains, specifically PEG in water and PDMS in n-heptane as the function of PEG content, provides important information regarding co-network morphology. According to the data shown in FIG. 12, the swelling of the PEG domain, $S_{H_2O,PEG}$ increases with PEG content and reaches saturation in the 24 to 32% PEG range. In this range the connectivity of the PEG phase reaches a limit and the co-network is unable to imbibe more water even with increasing PEG in the system. In contrast, $S_{C_7,PDMS}$ increases monotonically with decreasing PEG (increasing PDMS) content, and keeps increasing even beyond 240% measured at 16% PEG. These observations reflect the fact that the interaction parameter for PDMS/n-heptane is higher than that of PEG/water (i.e., the affinity of PDMS to n-heptane is higher than that of PEG to water).

As depicted in FIG. 12, the water and n-heptane swelling curves cross at approximately 36% PEG. This crossover occurs at much less than 50% PEG because of the detailed morphology of the co-networks investigated in FIG. 12. While not wishing to be bound to any one theory, it is probable that the crystalline PEG domains prevent the n-heptane-swollen rubbery PDMS domains from reaching the degree of swelling of a homo-PDMS network. Evidently, the amphiphilic co-networks investigated in FIG. 12 are crosslinked not only by covalently bonded domains but also by physical van der Waals forces, akin to thermoplastic elastomer networks. In the amphiphilic networks and/or co-networks used in conjunction with the insulin producing device the crystalline PEG is the hard domain and the n-heptane-swollen rubbery PDMS is the soft domain. By increasing the PEG content, the sizes/volumes of the hard PEG domains increase, and their contribution to the overall crosslink density of the network increases.

The membranes are optically clear when placed in both water and n-heptane, and remain clear during swelling indicating a nano-structured morphology in which the dimensions of the incompatible PEG and PDMS domains is less than about 400 nm (i.e., much less than the wave length of visible light).

Oxygen Permeability of Amphiphilic Co-Networks:

The oxygen permeability of the following co-networks from Table 2—APCN-24, APCN-32, and APCN-40—are determined by using the equipment and a methodology described below to measure the oxygen permeability of highly oxygen permeable membranes for various oxygen permeable-based applications.

The oxygen permeability of water-swollen membranes (usually expressed by Dk in barrer units) is a critical parameter of many materials, including contact lenses. According to various analyses, the internationally accepted Fatt method for the determination of oxygen permeabilities of hydrogels, is, however, unsuitable to determine Dk's above 100 barrers (see International Standard ISO 9913-1: 1996(E)). Accordingly, in order to determine precise Dk's values in the 100 to 800 barrer range the following method is utilized.

Figure 13:
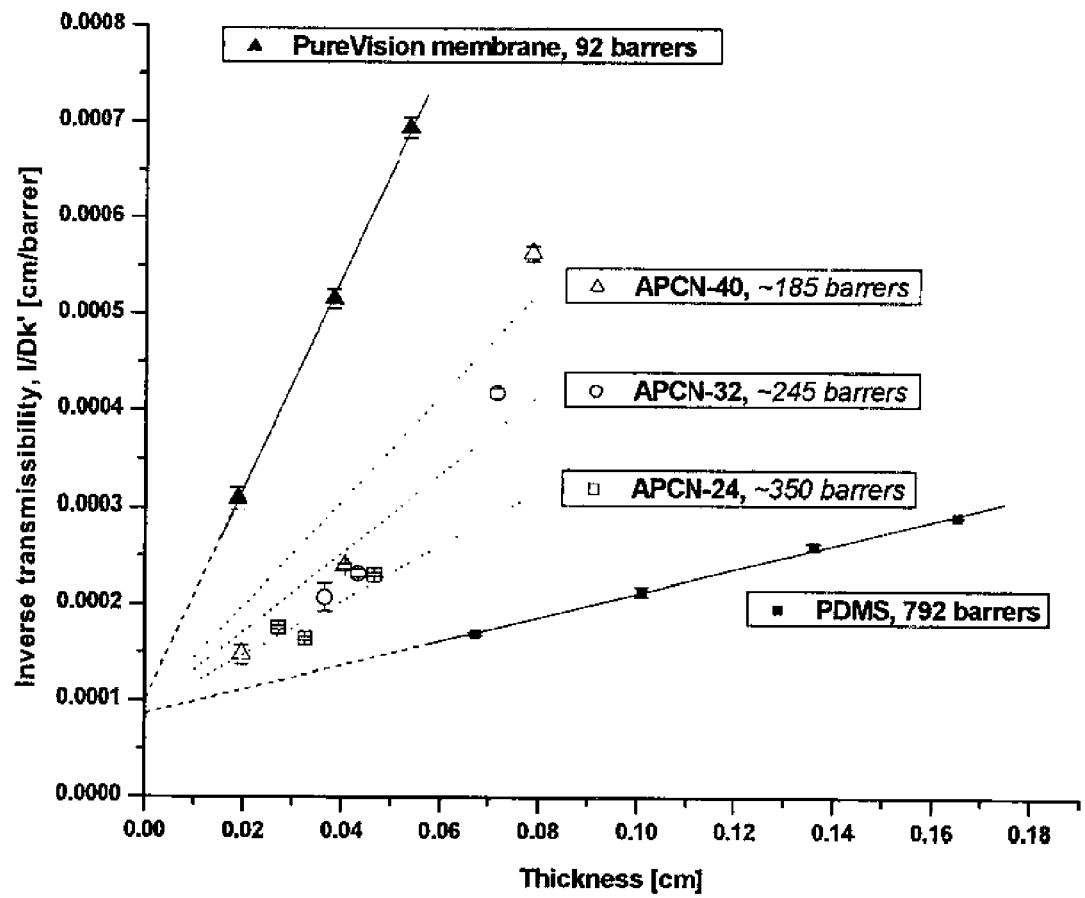
FIG. 13 is a series of plots that permit the calculation of the oxygen permeability of various amphiphilic co-networks made in accordance with one embodiment of the present invention.

The oxygen permeability of water-swollen membranes is obtained from the slopes of linear I/Dk' versus I plots (where Dk' is the apparent permeability and I membrane thickness). Table 3 shows experimental data, and FIG. 13 shows I/Dk' vs. I plots for a series of membranes; for comparison, FIG. 13 also shows a plot obtained with a PDMS membrane, whose permeability is determined to be 792 barrers, and a plot for a set of membranes used in extended-wear soft contact lenses (92 barrers, PureVision, Bausch & Lomb Co.). This data is used for comparison purposes to demonstrate the oxygen permeability of the networks and/or co-networks described above. In this instance, the following data is one possible manner by which to gauge the oxygen permeability of a network for use in conjunction with the insulin producing devices of the present invention. Other methods and/or tests could be used and as such, the present invention is not limited to solely to oxygen permeability testing method described herein.

TABLE 3

| Co-Network[a] | Apparent permeability, Dk', in barrer (thickness, in μm) | | |
|---|---|---|---|
| | Sample 1 | Sample 2 | Sample 3 |
| APCN-24 | 155 (272) | 197 (325) | 202 (465) |
| APCN-32 | 176 (375) | 186 (432) | 171 (714) |
| APCN-40 | 133 (196) | 170 (406) | 140 (785) |
| PureVision | 60.8 (188) | 73.9 (381) | 77.3 (536) |

[a]The digits indicate the % PEG content in the amphiphilic co-networks.

The procedure of casting membranes of various thicknesses is described above.

To obtain an estimate of oxygen permeabilities of the co-networks listed in Table 3, the apparent oxygen permeabilities (Dk's) are determined for membranes prepared in the 0.02 to 0.08 cm thickness range. The diffusional resistance of the boundary layer is set at 0.00009 cm/barrer (see the intercept on the y axis in FIG. 9), a value characteristic of for the instrument used. This value does not vary much in the 100 to 800 barrer range, and therefore obtaining it by the indicated linear regression is acceptable. The slopes of the dotted lines yield Dk=approximately 350, Dk=approximately 245, and Dk=approximately 185 barrers for APCN-24, APCN-32, and APCN-40, respectively. As shown by the Dk' values in Table 1, the apparent oxygen permeabilities of one example of these co-networks are 2 to 3 times higher than those of contemporary extended wear soft contact lens hydrogels. These values indicate that the oxygen permeabilities of co-networks formed in accordance with the amphiphilic networks and/or co-networks of the insulin producing device are far above those ever reported for hydrogels.

Figure 14:
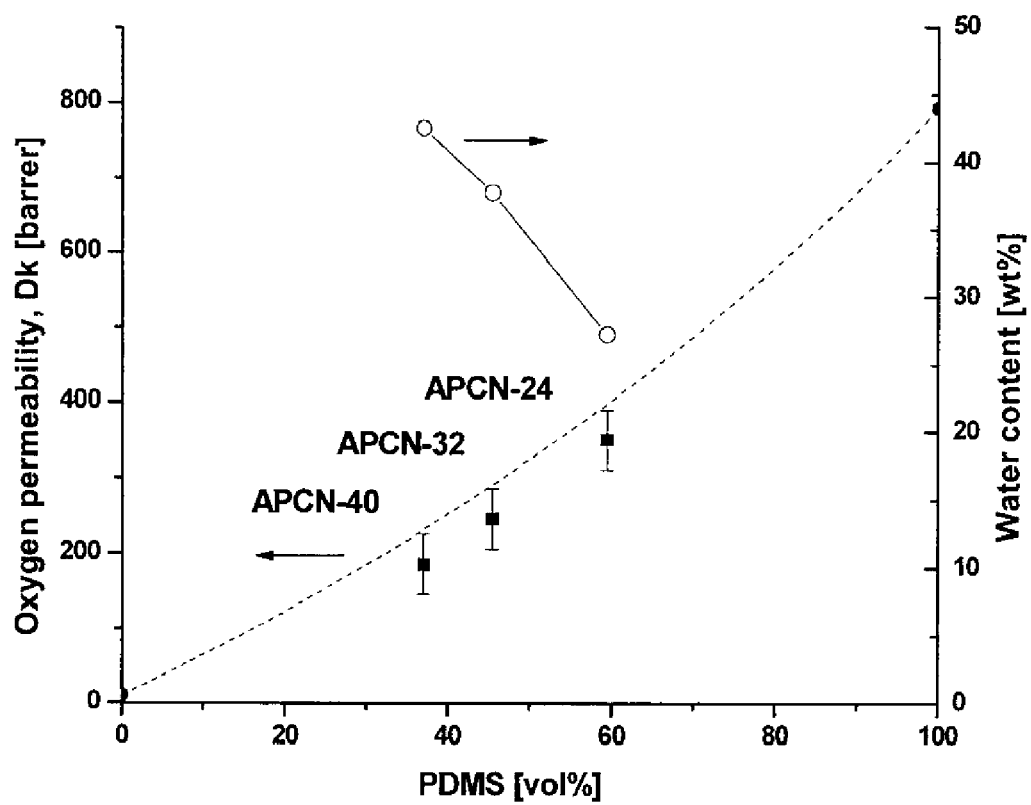
FIG. 14 is a graph of the oxygen permeabilities and water contents as a function of the PDMS volume fraction in water-swollen amphiphilic co-networks made in accordance with one embodiment of the present invention.

FIG. 14 shows the effect of PDMS content on the oxygen permeability of the three co-networks listed in Table 3. The solid line indicates the water content of the amphiphilic networks and/or co-networks used in conjunction with the insulin producing device's co-networks. The dashed line indicates the maximum permeability of an "ideal" PDMS/hydrogel co-network in which the PDMS phase is continuous over the entire composition range, is calculated by the following formulas:

$$P = P_1 \frac{(P_2 + 2P_1 - 2V_2(P_1 - P_2))}{(P_2 + 2P_1 + V_2(P_1 - P_2))}$$

where $P_1$ is the permeability of PDMS, $P_2$ is the permeability of the hydrogel (water-swollen PEG), and $V_2$ is the volume fraction of the PDMS. The apparent oxygen permeabilities of the membranes formed from the co-networks listed in Table 3 are not much below the theoretical maximum permeabilities. According to the data, the co-networks used in conjunction with the insulin producing device are essentially bi-continuous even at relatively low PDMS contents.

Mechanical Properties of the Amphiphilic Co-Networks:

The tensile strength properties of water-swollen membranes are determined by using an Instron 5567 (20 N load cell) equipped with a mechanical extensometer at a crosshead speed of 5 mm/min. Microdumbells were die-cut according to ASTM 638-V (i.e., gauge length 7.62 mm, width 3.18 mm). Sample thickness is measured by a micrometer. Tensile strength properties of two or three specimens of each of the co-networks (co-networks APCN-16, APCN-24, APCN-32, and APCN-40) are determined and averaged.

Figure 15:
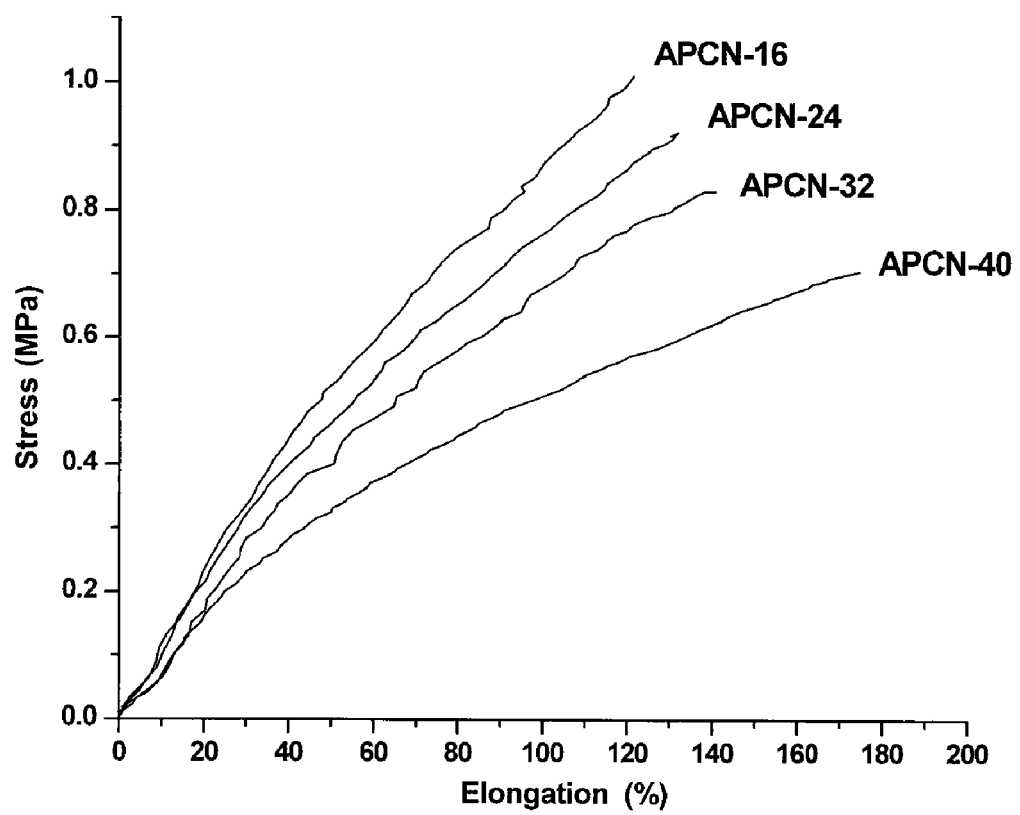
FIG. 15 is a graph of the stress-strain curves of various water-swollen amphiphilic co-networks made in accordance with one embodiment of the present invention.

FIG. 15 shows the stress/strain profiles of a series of water-swollen amphiphilic co-networks (co-networks APCN-16, APCN-24, APCN-32, and APCN-40). Table 4 summarizes the mechanical properties of these water swollen co-networks.

TABLE 4

| Co-Network | Tensile Strength [MPa] | Elongation [%] | Modulus [MPa] |
|---|---|---|---|
| APCN-16 | 1.00 | 118 | 1.10 |
| APCN-24 | 0.91 | 132 | 0.98 |
| APCN-32 | 0.84 | 140 | 0.90 |
| APCN-40 | 0.71 | 175 | 0.67 |

As can be seen from the data above, the tensile strengths and elongation percentage decrease with increasing PEG content, whereas the moduli show an increase with increasing PEG content. These trends are in line with overall co-network compositions, and reflect the effect of the swelling of the PEG phase on the mechanical properties. Remarkably, the tensile strength of even the APCN-40 (i.e., the co-network with 40% PEG) is superior to an unfilled PDMS network of the same molecular weight between crosslink points ($M_c$) and crosslink density (0.6 MPa). Overall, these properties are sufficient or even surpass the requirements for biological, including ophthalmic, applications.

Thermal Behavior Properties of the Amphiphilic Co-Networks:

DSC scans are performed by a DuPont 2100 thermal analyzer under a nitrogen atmosphere with a heating rate of 10° C./min. The first order (melting) transition is the minimum of the DSC endotherm. Glass-transition temperatures ($T_g$'s) are obtained after two heating/cooling cycles by the use of the midpoint method.

Figure 16:
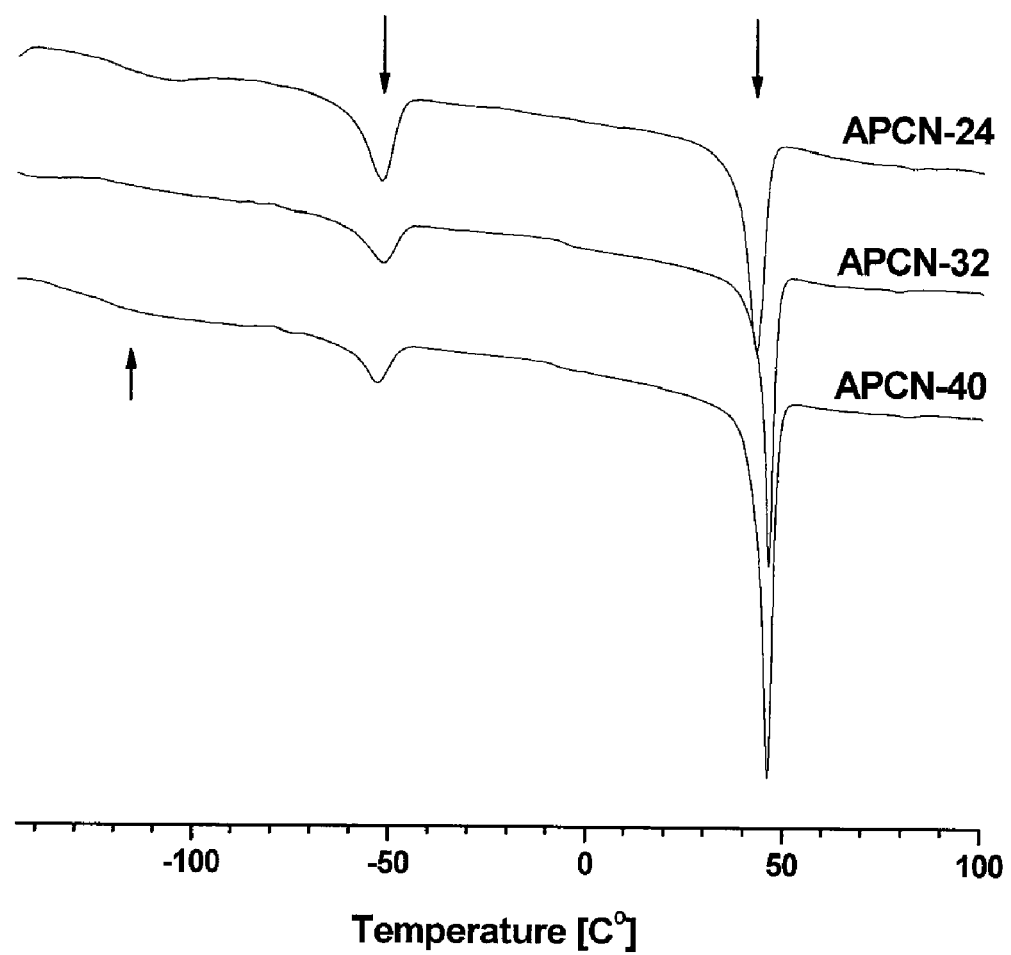
FIG. 16 is a plot of the DSC traces of PEG/PDMS amphiphilic co-networks, where the up arrow indicates the glass transition temperature of PDMS and the down arrows indicate melting peaks of the PDMS and PEG phases.

FIG. 16 shows the DSC scans of three amphiphilic co-networks of different PEG contents as listed therein. The traces indicate two first order (melting) transitions: one at −52° C. associated with the crystalline PDMS phase and another at approximately 46° C. due to the crystalline PEG phase. The latter transition reflects the melting of PEG segments of $M_n$=4.6 kg/mol, and is significantly lower than 62° C., the melting point of PEG of the same $M_n$. While not wishing to be bound to any one theory, this shift to lower temperatures occurs because the PEG segments are covalently linked to the soft PDMS phases. Although the molecular weights between crosslink points ($M_c$'s) of the PEG segments are the same in all three co-networks, the softening effect appears to be stronger with the co-network containing the least amount of PEG (APCN-24). The degree of crystallinity of the PEG domains in the co-networks is approximately 30% (i.e., much less than of pure PEG (70%)). While not wishing to be bound to any one theory, this is also due to the covalently bonded PDMS segments.

The second order transition ($T_g$'s) of the PDMS phase is discernible in the range of −125° C. to −100° C., however, the glass transition of the non-crystalline PEG could not be identified.

In light of the above results, in amphiphilic co-networks used in conjunction with the insulin producing device swelling in water increase with the PEG content, whereas in n-heptane the trend is reversed. The PEG domains become continuous with approximately 13% PEG, and co-continuity/bipercolation is evident over a wide composition range. Co-networks swollen with n-heptane are combinations of two networks: one held together by covalent linkages between different domains, and the other by physical forces akin to thermoplastic elastomers. The oxygen permeabilities of the co-networks of the amphiphilic networks and/or co-networks used in conjunction with the insulin producing device are far superior to similar materials currently available, one example being commercial extended-wear soft contact lens membranes. The mechanical properties of water-swollen co-networks reflect their overall compositions and are deemed appropriate for biological application.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. An implantable device for providing insulin comprising:
    at least one spacing member having a suitable thickness, a first face, and a second face, wherein the first face and second face are positioned opposed to one another;
    a first immunoisolatory membrane affixed to the first face of the at least one spacing member;
    and a second immunoisolatory membrane affixed to the second face of the at least one spacing member;
    wherein the first immunoisolatory membrane and second immunoisolatory membrane are amphiphilic membranes having pore dimensions in the range of about 3.0 nm to 4.0 nm, wherein the amphiphilic membranes are comprised of polyethylene glycol polymer and polydimethylsiloxane polymer strands crosslinked by bis(dimethylsilyloxy)ethoxydimethylsilyloxy phenylsilane to form an amphiphilic network, wherein the affixing of the first immunoisolatory membrane and the second immunoisolatory membrane to the at least one spacing member defines an internal volume bounded by the at least one spacing member, the first immunoisolatory membrane and the second immunoisolatory membrane, the internal volume holding insulin producing cells suspended in the amphiphilic network, wherein the amphiphilic network has a tensile strength in the range of about 0.5 MPa to about 3.0 MPa and an elongation in the range of about 50% to about 600%.

2. The device of claim 1, wherein the insulin producing cells are porcine endocrine cells.

3. The device of claim 1, wherein the distance between the first immunoisolatory membrane and the second immunoisolatory membrane is in the range of about 500 microns to about 700 microns.

4. The device of claim 1, wherein the spacing member contains one or more ports designed to permit filling and maintenance of the internal volume.

5. The device of claim 1, wherein the spacing member contains one or more vents.

6. The device of claim 1, wherein the amphiphilic membrane is prepared by:
    (i) providing styryl-telechelic polyethylene glycol end-functionalized by hydrosilation with bis(dimethylsilyloxy)ethoxydimethylsilyloxy phenylsilane;
    (ii) further hydrosilating the end functionalized styryl-telechelic polyethylene glycol by vinyl-telechelic polydimethylsiloxane to create a diblock polymer;
    (iii) purifying the resulting diblock polymer; and
    (iv) adding at least one acid to the purified diblock polymer.

7. The device of claim 1, wherein the first immunoisolatory membrane and second immunoisolatory membrane are amphiphilic water swollen membranes having bi-continuous hydrophilic pore dimensions in the range of about 3.0 nm to about 4.0 nm.

8. A method of using the device of claim 1, comprising the steps of:
    implanting the device of claim 1 into a diabetic mammal; and
    filling the internal volume of said device with insulin producing cells suspended in the amphiphilic network.

9. The method of claim 8, wherein the device is implanted in subcutaneous loci.

10. The method of claim 8, wherein the device is implanted in intraperitoneal loci.

11. A method of using the device of claim 7, comprising the steps of:
    implanting the device of claim 7 into a diabetic mammal; and
    filling the internal volume of said device with insulin producing cells suspended in the amphiphilic network.

12. The method of claim 11, wherein the device is implanted in subcutaneous loci.

13. The method of claim 11, wherein the device is implanted in intraperitoneal loci.

14. An implantable device for providing insulin comprising:
    (i) cells for the production of insulin, and
    (ii) an amphiphilic membrane that allows the for the passage of said insulin, wherein the amphiphilic membrane has pore dimensions in the range of about 3.0 nm to 4.0 nm, wherein the amphiphilic membranes are comprised of polyethylene glycol and polydimethylsiloxane polymer strands crosslinked by bis(dimethylsilyloxy) ethoxydimethylsilyloxy phenylsilane to form an amphiphilic network, wherein the amphiphilic network has a tensile strength in the range of about 0.5 MPa to about 3.0 MPa and an elongation in the range of about 50% to about 600%, and wherein the bis(dimethylsilyloxy) ethoxydimethylsilyloxy phenylsilane is a chain extender that also functions as a crosslinker.

15. The device of claim 14, wherein the insulin producing cells are porcine endocrine cells.

16. The device of claim 14, wherein the implantable device contains one or more vents.

17. The device of claim 14, where the amphiphilic membrane is produced by first preparing a functional multiblock polymer and then crosslinking the functional multiblock polymer.

18. The device of claim 17, where the functional multiblock polymer is produced by hydrosilation.

19. The device of claim 17, where the functional multiblock polymer is crosslinked by a condensation reaction.

* * * * *